(12) United States Patent
Sohn

(10) Patent No.: US 10,893,927 B2
(45) Date of Patent: Jan. 19, 2021

(54) INFERIOR VENA CAVA BLOOD-FLOW IMPLANT

(71) Applicant: MAGENTA MEDICAL LTD., Kadima (IL)

(72) Inventor: Zev Sohn, Ginot Shomron (IL)

(73) Assignee: MAGENTA MEDICAL LTD., Kadima (IL)

( * ) Notice: Subject to any disclaimer, the term of this patent is extended or adjusted under 35 U.S.C. 154(b) by 0 days.

(21) Appl. No.: 16/035,871

(22) Filed: Jul. 16, 2018

(65) Prior Publication Data
US 2019/0298509 A1 Oct. 3, 2019

Related U.S. Application Data

(60) Provisional application No. 62/649,788, filed on Mar. 29, 2018.

(51) Int. Cl.
*A61F 2/82* (2013.01)
*A61F 2/24* (2006.01)
(Continued)

(52) U.S. Cl.
CPC .......... *A61F 2/06* (2013.01); *A61B 17/12036* (2013.01); *A61B 17/12109* (2013.01);
(Continued)

(58) Field of Classification Search
CPC ...... A61F 2/2418; A61F 2/2427; A61F 2/246; A61F 2/2463; A61F 2230/0054;
(Continued)

(56) References Cited

U.S. PATENT DOCUMENTS 4,919,647 A 4/1990 Nash
4,954,055 A 9/1990 Raible et al.
(Continued)

FOREIGN PATENT DOCUMENTS

AU 2013205145 A1 5/2013
CN 1219136 A 6/1999
(Continued)

OTHER PUBLICATIONS

Non-Final Office Action for U.S. Appl. No. 15/888,771, dated Oct. 4, 2019.
(Continued)

*Primary Examiner* — Ann Schillinger
(74) *Attorney, Agent, or Firm* — Dorsey & Whitney LLP

(57) ABSTRACT

An inferior vena cava (IVC) implant is provided that includes a tubular implant body, which is configured to assume a compressed delivery configuration and an expanded deployment configuration, and configured such that when implanted in the expanded deployment configuration in the IVC in the vicinity of the renal junctions, (a) has a generally tubular shape, (b) has upstream and downstream ends, and (c) is shaped so as to define: (i) two indentations on opposite sides of the tubular implant body, which are shaped so as to allow blood flow in the two indentations from upstream of the tubular implant body to downstream of the tubular implant body, and (ii) one or more surfaces that at least partially block blood flow through an interior of the tubular implant body from upstream of the tubular implant body to downstream of the tubular implant body. Other embodiments are also described.

24 Claims, 8 Drawing Sheets

(51) Int. Cl.
    *A61M 27/00* (2006.01)
    *A61F 2/06* (2013.01)
    *A61B 17/12* (2006.01)
(52) U.S. Cl.
    CPC .......... *A61F 2/82* (2013.01); *A61F 2002/068* (2013.01); *A61F 2210/0014* (2013.01); *A61F 2220/0016* (2013.01); *A61F 2230/0067* (2013.01); *A61F 2230/0095* (2013.01); *A61F 2250/0098* (2013.01)
(58) Field of Classification Search
    CPC .................. A61F 2/24; A61F 2002/018; A61F 2230/0017; A61F 2230/006; A61F 2230/0067; A61F 2230/0071; A61F 2230/008; A61F 2230/0093; A61F 2250/001; A61F 2/07; A61F 2/2475; A61F 2002/30187
    See application file for complete search history.

(56) References Cited

U.S. PATENT DOCUMENTS

| | | | |
|---|---|---|---|
| 5,613,935 A | 3/1997 | Jarvik | |
| 5,713,730 A | 2/1998 | Nose et al. | |
| 5,749,855 A | 5/1998 | Reitan | |
| 5,772,693 A | 6/1998 | Brownlee | |
| 5,876,385 A | 3/1999 | Ikari et al. | |
| 5,964,694 A | 10/1999 | Siess et al. | |
| 6,086,527 A | 7/2000 | Talpade | |
| 6,135,729 A | 10/2000 | Aber | |
| 6,247,892 B1 | 6/2001 | Kazatchkov et al. | |
| 6,482,228 B1 | 11/2002 | Norred | |
| 6,533,716 B1 | 3/2003 | Schmutz-Rode et al. | |
| 6,592,567 B1 | 7/2003 | Levin et al. | |
| 6,616,624 B1 | 9/2003 | Kieval | |
| 6,884,210 B2 | 4/2005 | Nose et al. | |
| 7,004,925 B2 | 2/2006 | Navia et al. | |
| 7,144,364 B2 | 12/2006 | Barbut et al. | |
| 7,159,593 B2 | 1/2007 | McCarthy et al. | |
| 7,201,772 B2 | 4/2007 | Schwammenthal et al. | |
| 7,335,192 B2 | 2/2008 | Keren et al. | |
| 7,341,570 B2 | 3/2008 | Keren et al. | |
| 7,485,104 B2 | 2/2009 | Kieval | |
| 7,717,952 B2 | 5/2010 | Case et al. | |
| 7,744,642 B2 | 6/2010 | Rittgers et al. | |
| 7,762,941 B2 | 7/2010 | Jarvik | |
| 7,766,853 B2 | 8/2010 | Lane | |
| 7,766,892 B2 | 8/2010 | Keren et al. | |
| 7,766,961 B2 | 8/2010 | Patel et al. | |
| 7,780,628 B1 | 8/2010 | Keren et al. | |
| 7,811,221 B2 | 10/2010 | Gross | |
| 7,841,976 B2 | 11/2010 | McBride et al. | |
| 7,914,503 B2 | 3/2011 | Goodson et al. | |
| 8,012,121 B2 | 9/2011 | Goodson et al. | |
| 8,079,948 B2 | 12/2011 | Shifflette | |
| 8,221,492 B2 | 7/2012 | Case et al. | |
| 8,235,933 B2 | 8/2012 | Keren et al. | |
| 8,277,470 B2 | 10/2012 | Demarais et al. | |
| 8,376,707 B2 | 2/2013 | Mcbride et al. | |
| 8,449,443 B2 | 5/2013 | Rodefeld et al. | |
| 8,512,262 B2 | 8/2013 | Gertner | |
| 8,538,535 B2 | 9/2013 | Ariav et al. | |
| 8,579,858 B2 | 11/2013 | Reitan et al. | |
| 8,617,239 B2 | 12/2013 | Reitan | |
| 8,690,749 B1 | 4/2014 | Nunez | |
| 8,734,331 B2 | 5/2014 | Evans et al. | |
| 8,734,508 B2 | 5/2014 | Hastings et al. | |
| 8,777,832 B1 | 7/2014 | Wang et al. | |
| 8,849,398 B2 | 9/2014 | Evans | |
| 9,028,216 B2 | 5/2015 | Schumacher et al. | |
| 9,138,518 B2 | 9/2015 | Campbell et al. | |
| 9,162,017 B2 | 10/2015 | Evans et al. | |
| 9,314,558 B2 | 4/2016 | Er | |
| 9,358,329 B2 | 6/2016 | Fitzgerald et al. | |
| 9,597,205 B2 | 3/2017 | Tuval | |
| 9,764,113 B2 | 9/2017 | Tuval et al. | |
| 9,913,937 B2 | 3/2018 | Schwammenthal et al. | |
| 10,039,874 B2 | 8/2018 | Schwammenthal et al. | |
| 10,231,838 B2 * | 3/2019 | Chin ................... A61F 2/2475 |
| 10,245,363 B1 | 4/2019 | Rowe | |
| 10,583,231 B2 | 3/2020 | Schwammenthal et al. | |
| 10,799,626 B2 | 10/2020 | Siess et al. | |
| 2002/0107536 A1 | 8/2002 | Hussein | |
| 2003/0055486 A1 | 3/2003 | Adams et al. | |
| 2004/0064090 A1 | 4/2004 | Keren et al. | |
| 2004/0064091 A1 | 4/2004 | Keren et al. | |
| 2004/0111006 A1 | 6/2004 | Alferness et al. | |
| 2004/0116769 A1 | 6/2004 | Jassawalla et al. | |
| 2004/0167415 A1 | 8/2004 | Gelfand et al. | |
| 2004/0210236 A1 | 10/2004 | Allers et al. | |
| 2004/0260389 A1 | 12/2004 | Case et al. | |
| 2005/0033406 A1 | 2/2005 | Barnhart et al. | |
| 2005/0049692 A1 | 3/2005 | Numamoto et al. | |
| 2005/0055082 A1 | 3/2005 | Ben et al. | |
| 2005/0079274 A1 | 4/2005 | Palasis et al. | |
| 2005/0119682 A1 | 6/2005 | Nguyen et al. | |
| 2006/0106449 A1 | 5/2006 | Ben | |
| 2007/0100435 A1 | 5/2007 | Case et al. | |
| 2007/0162103 A1 | 7/2007 | Case et al. | |
| 2007/0208291 A1 | 9/2007 | Patel | |
| 2007/0260327 A1 | 11/2007 | Case et al. | |
| 2007/0293808 A1 * | 12/2007 | Williams ................... A61F 2/06 604/9 |
| 2008/0103591 A1 | 5/2008 | Siess | |
| 2008/0132748 A1 | 6/2008 | Shifflette | |
| 2008/0154236 A1 | 6/2008 | Elkins et al. | |
| 2008/0183280 A1 | 7/2008 | Agnew et al. | |
| 2009/0024195 A1 | 1/2009 | Rezai et al. | |
| 2009/0062597 A1 | 3/2009 | Shifflette | |
| 2009/0093796 A1 | 4/2009 | Pfeffer et al. | |
| 2009/0131785 A1 | 5/2009 | Lee et al. | |
| 2009/0264991 A1 | 10/2009 | Paul et al. | |
| 2009/0287299 A1 | 11/2009 | Tabor et al. | |
| 2009/0318857 A1 | 12/2009 | Goodson et al. | |
| 2010/0130810 A1 | 5/2010 | Mohl | |
| 2011/0004046 A1 | 1/2011 | Campbell et al. | |
| 2011/0106244 A1 | 5/2011 | Ferrari et al. | |
| 2011/0152999 A1 | 6/2011 | Hastings et al. | |
| 2011/0190874 A1 | 8/2011 | Celermajer et al. | |
| 2011/0213408 A1 | 9/2011 | Gross et al. | |
| 2011/0230949 A1 | 9/2011 | Haverkost et al. | |
| 2011/0257462 A1 | 10/2011 | Rodefeld et al. | |
| 2011/0264075 A1 | 10/2011 | Leung et al. | |
| 2011/0282128 A1 | 11/2011 | Reitan et al. | |
| 2011/0301662 A1 | 12/2011 | Bar-Yoseph et al. | |
| 2012/0022579 A1 | 1/2012 | Fulton | |
| 2012/0059460 A1 | 3/2012 | Reitan | |
| 2012/0089047 A1 | 4/2012 | Ryba et al. | |
| 2012/0116382 A1 | 5/2012 | Ku et al. | |
| 2012/0130469 A1 | 5/2012 | Cragg et al. | |
| 2012/0172654 A1 | 7/2012 | Bates | |
| 2012/0224970 A1 | 9/2012 | Schumacher et al. | |
| 2012/0237357 A1 | 9/2012 | Schumacher et al. | |
| 2013/0053623 A1 | 2/2013 | Evans et al. | |
| 2013/0053732 A1 | 2/2013 | Heuser | |
| 2013/0079874 A1 | 3/2013 | Doss et al. | |
| 2013/0177409 A1 | 7/2013 | Schumacher et al. | |
| 2013/0177432 A1 | 7/2013 | Toellner et al. | |
| 2014/0018840 A1 | 1/2014 | Morgan et al. | |
| 2014/0025041 A1 | 1/2014 | Fukuoka et al. | |
| 2014/0128659 A1 | 5/2014 | Heuring et al. | |
| 2014/0275722 A1 | 9/2014 | Zimmermann et al. | |
| 2014/0350658 A1 | 11/2014 | Benary et al. | |
| 2015/0018597 A1 | 1/2015 | Fierens et al. | |
| 2015/0119633 A1 | 4/2015 | Haselby et al. | |
| 2015/0157777 A1 | 6/2015 | Tuval et al. | |
| 2015/0164662 A1 | 6/2015 | Tuval | |
| 2015/0176582 A1 | 6/2015 | Liebing | |
| 2015/0343136 A1 | 12/2015 | Nitzan et al. | |
| 2015/0343186 A1 | 12/2015 | Nitzan et al. | |
| 2016/0022890 A1 | 1/2016 | Schwammenthal et al. | |
| 2016/0051741 A1 | 2/2016 | Schwammenthal et al. | |
| 2016/0053768 A1 | 2/2016 | Schumacher et al. | |

(56) References Cited

U.S. PATENT DOCUMENTS

| | | | |
|---|---|---|---|
| 2016/0136343 | A1 | 5/2016 | Anagnostopoulos |
| 2016/0279310 | A1 | 9/2016 | Scheckel et al. |
| 2017/0071769 | A1 | 3/2017 | Mangiardi |
| 2017/0100527 | A1 | 4/2017 | Schwammenthal et al. |
| 2018/0126130 | A1 | 5/2018 | Nitzan et al. |
| 2018/0149165 | A1 | 5/2018 | Siess et al. |
| 2018/0303993 | A1 | 10/2018 | Schwammenthal et al. |

FOREIGN PATENT DOCUMENTS

| | | | |
|---|---|---|---|
| EP | 3108909 | A1 | 12/2016 |
| JP | 2012505038 | A | 3/2012 |
| WO | 90/13321 | | 11/1990 |
| WO | 1994/01148 | A1 | 1/1994 |
| WO | 9744071 | A1 | 11/1997 |
| WO | 99/34847 | | 7/1999 |
| WO | 2001/083016 | A2 | 5/2000 |
| WO | 2002/070039 | A2 | 3/2001 |
| WO | 0183016 | A2 | 11/2001 |
| WO | 2002/38085 | A1 | 5/2002 |
| WO | 2002038085 | | 5/2002 |
| WO | 03/006096 | | 1/2003 |
| WO | 04073796 | | 2/2003 |
| WO | 03103745 | A2 | 12/2003 |
| WO | 2004073796 | A2 | 9/2004 |
| WO | 2005020848 | A2 | 3/2005 |
| WO | 2007127477 | A2 | 11/2007 |
| WO | 2008005747 | A2 | 1/2008 |
| WO | 2008055301 | A1 | 5/2008 |
| WO | 2009010963 | A2 | 1/2009 |
| WO | 2009091965 | A1 | 7/2009 |
| WO | 2009129481 | A1 | 10/2009 |
| WO | 2010150208 | A2 | 12/2010 |
| WO | 2011035926 | A1 | 3/2011 |
| WO | 2011076441 | A1 | 6/2011 |
| WO | 2012007141 | A1 | 1/2012 |
| WO | 2013032849 | A1 | 3/2013 |
| WO | 2013148697 | A1 | 10/2013 |
| WO | 2013183060 | A2 | 12/2013 |
| WO | 2014141284 | A2 | 9/2014 |
| WO | 2015063277 | A2 | 5/2015 |
| WO | 2015177793 | A2 | 11/2015 |
| WO | 2016185473 | A1 | 11/2016 |
| WO | 2018061001 | A2 | 4/2018 |
| WO | 2018061002 | A1 | 4/2018 |
| WO | 2018220589 | A1 | 12/2018 |

OTHER PUBLICATIONS

U.S. Appl. No. 16/677,893, filed Nov. 8, 2019.
U.S. Appl. No. 16/682,016, filed Nov. 13, 2019.
Corrected Notice of Allowance for U.S. Appl. No. 15/423,368 dated Apr. 17, 2019.
European Search Report for European Application No. 14762232.8 dated Sep. 28, 2016.
Final Office Action for U.S. Appl. No. 14/931,363 dated Jun. 1, 2017.
Final Office Action for U.S. Appl. No. 15/312,034 dated Jan. 17, 2019.
International Search Report and Written Opinion for International Application No. PCT/IL2016/050525 dated Oct. 14, 2016.
International Search Report and Written Opinion from International Application No. PCT/IL2017/051092 dated Jan. 16, 2018.
International Search Report and Written Opinion from International Application No. PCT/IL2017/051273 dated Apr. 17, 2018.
Invitation to pay additional fees for International Application No. PCT/IL2015/050532 dated Nov. 17, 2015.
Issue Notification for U.S. Appl. No. 14/931,363 dated Feb. 21, 2018.
Issue Notification for U.S. Appl. No. 16/022,445 dated Jul. 10, 2019.
Non-Final Office Action for U.S. Appl. No. 14/405,144 dated Feb. 22, 2016.
Non-Final Office Action for U.S. Appl. No. 14/405,144 dated Jul. 14, 2016.
Non-Final Office Action for U.S. Appl. No. 14/567,439 dated Nov. 16, 2016.
Non-Final Office Action for U.S. Appl. No. 14/774,081 dated May 24, 2017.
Non-Final Office Action for U.S. Appl. No. 14/774,081 dated Oct. 12, 2017.
Non-Final Office Action for U.S. Appl. No. 14/931,363 dated Feb. 15, 2017.
Non-Final Office Action for U.S. Appl. No. 14/931,363 dated Oct. 3, 2016.
Non-Final Office Action for U.S. Appl. No. 15/423,368 dated Jun. 6, 2018.
Non-Final Office Action for U.S. Appl. No. 16/022,445 dated Aug. 9, 2018.
Notice of Allowance for U.S. Appl. No. 14/567,439 dated Jun. 2, 2017.
Notice of Allowance for U.S. Appl. No. 14/774,081 dated Apr. 11, 2018.
Notice of Allowance for U.S. Appl. No. 14/931,363 dated Dec. 12, 2017.
Notice of Allowance for U.S. Appl. No. 14/931,363 dated Oct. 12, 2017.
Notice of Allowance for U.S. Appl. No. 15/312,034 dated Jun. 27, 2019.
Notice of Allowance for U.S. Appl. No. 15/423,368 dated Apr. 4, 2019.
Notice of Allowance for U.S. Appl. No. 15/423,368 dated Nov. 13, 2018.
Notice of Allowance for U.S. Appl. No. 16/022,445 dated Mar. 18, 2019.
Office Action for Chinese Patent Application No. 201380037335.4 dated Mar. 22, 2017.
Office Action for Chinese Patent Application No. 201380037335.4 dated Sep. 20, 2017.
Office Action for Japanese Patent Application No. 2015-562562 dated Jun. 13, 2018.
Office Action for Japanese Patent Application No. 2015562562 dated Oct. 27, 2017.
Restriction Requirement for U.S. Appl. No. 14/567,439 dated Aug. 23, 2016.
Restriction Requirement for U.S. Appl. No. 14/774,081 dated Mar. 9, 2017.
Restriction Requirement for U.S. Appl. No. 14/931,363 dated Jul. 22, 2016.
Restriction Requirement for U.S. Appl. No. 15/888,771 dated Apr. 15, 2019.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/423,368, filed Feb. 2, 2017.
U.S. Appl. No. 16/022,445, filed Jun. 28, 2018.
U.S. Appl. No. 16/273,898, filed Feb. 12, 2019.
U.S. Appl. No. 16/278,323, filed Feb. 18, 2019.
U.S. Appl. No. 16/281,385, filed Feb. 21, 2019.
U.S. Appl. No. 16/345,389, filed Apr. 26, 2019.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/425,814, filed Nov. 23, 2016.
U.S. Appl. No. 62/401,403 dated Sep. 29, 2016.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.

(56) References Cited

OTHER PUBLICATIONS

Fraser, et al., "The use of computational fluid dynamics in the development of ventricular assist devices", Medical engineering & physics, 33.3, 2011, pp. 263-280.
Hsu, et al., "Review of recent patents on foldable ventricular assist devices", Recent Patents on Biomedical Engineering, 5.3, 2012, pp. 208-222.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Reul, et al., "Blood pumps for circulatory support", Perfusion-Sevenoaks, 15.4, 2000, pp. 295-312.
Song, et al., "Axial flow blood pumps", ASAIO journal, 49, 2003, pp. 355-364.
Throckmorton, et al., "Design of a protective cage for an intravascular axial flow blood pump to mechanically assist the failing Fontan", Artificial organs, 33.8, 2009, pp. 611-621.
Thunberg, et al., "Ventricular assist devices today and tomorrow", Journal of cardiothoracic and vascular anesthesia, 24.4, 2010, pp. 656-680.
Timms, , "A review of clinical ventricular assist devices", Medical engineering & physics, 33.9, 2011, pp. 1041-1047.
Wu, et al., "Design and simulation of axial flow maglev blood pump", International Journal of Information Engineering and Electronic Business, 3.2, 2011, p. 42.
Communication for European Application No. 15753493.4 dated Jul. 17, 2019.
European Search Report for European Application No. 13800935 dated Jan. 12, 2016.
International Search Report and Written Opinion for International Application No. PCT/IL2015/050532 dated Jan. 27, 2016.
International Search Report and Written Opinion for International Application No. PCT/IL2013/050495 dated Nov. 22, 2013.
International Search Report and Written Opinion for International Application No. PCT/IL2014/050289 dated Sep. 11, 2014.
International Search Report and Written Opinion from International Application No. PCT/IL2019/050334 dated Jun. 17, 2019.
Issue Notification for U.S. Appl. No. 15/423,368 dated May 8, 2019.
Office Action for Australian Application No. 2015262870 dated Apr. 29, 2019.
Office Action for Australian Application No. 2019202647 dated Jun. 26, 2019.
Office Action for Chinese Application No. 201380037335.4 dated Oct. 17, 2016.
Office Action for European Application No. 13800935 dated Sep. 30, 2016.
Office Action for Japanese Application No. 2015/562562 dated Jan. 29, 2019.
Office Action for Japanese Application No. 2016/568548 dated Mar. 18, 2019.
Burnett, et al., "Renal Interstitial Pressure and Sodium Excretion During Renal Vein Constriction", American Physiological Society, 1980, pp. F279-F282.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion And The Association With Renal Impairment In Patients With Cardiac Dysfunction", European Journal of Heart Failure, vol. 9, 2007, pp. 872-878.
Damman, et al., "Increased Central Venous Pressure Is Associated With Impaired Renal Function And Mortality In A Broad Spectrum Of Patients With Cardiovascular Disease", Journal of American College of Cardiology, vol. 53, 2009, pp. 582-588.
Doty, et al., "The Effect Of Increased Renal Venous Pressure On Renal Function", The Journal of Trauma,, vol. 47(6), Dec. 1999, pp. 1000-1003.
Felker, et al., "Anemia As A Risk Factor And Therapeutic Target In Heart Failure", Journal of the American College of Cardiology, vol. 44, 2004, pp. 959-966.
Firth, et al., "Raised Venous Pressure: A Direct Cause Of Sodium Retention In Oedema?", The Lancet, May 7, 1988, pp. 1033-1036.
Forman, et al., "Incidence, Predictors At Admission, And Impact Of Worsening Renal Function Among Patients Hospitalized With Heart Failure", Journal of American College of Cardiology, vol. 43, 2004, pp. 61-67.
Gomes, et al., "Heterologous Valve Implantation In The Infra-Renal Vena Cava For Treatment Of The Iliac Venous Valve Regurgitation Disease: Experimental Study", Rev Bras Cir Cardiovasc, vol. 17(4), 2002, pp. 367-369.
Haddy, et al., "Effect of Elevation Of Intraluminal Pressure On Renal Vascular Resistance", Circulation Research Journal Of The American Heart Association, vol. 4, 1956, pp. 659-663.
Heywood, et al., "High Prevalence Of Renal Dysfunction And Its Impact On Outcome In 118,465 Patients Hospitalized With Acute Decompensated Heart Failure: A Report From The ADHERE Database", Journal of Cardiac Failure, vol. 13, 2007, pp. 422-430.
Hillege, et al., "Renal Function As A Predictor Of Outcome In A Broad Spectrum Of Patients With Heart Failure", Circulation Journal of the American Heart Association, vol. 113, 2006, pp. 671-678.
Hillege, et al., "Renal Function, Neurohormonal Activation, And Survival In Patients With Chronic Heart Failure", Circulation Journal of the American Heart Association, vol. 102, 2000, pp. 203-210.
Ikari, "The Physics Of Guiding Catheter; The IKARI Guiding Catheter In TRI", available at httu:i /www.docstoc.com/docs/148136553/The-[KARI-catheter---anovel-guide-for-TRI--, uploaded on Mar. 8, 2013.
Lauten, et al., "Heterotopic Transcatheter Tricuspid Valve Implantation: First-In-Man Application Of A Novel Approach To Tricuspid Regurgitation", European Heart Journal, (1-7 as printed), Feb. 15, 2011, pp. 1207-1213.
McAlister, et al., "Renal Insufficiency And Heart Failure: Prognostic And Therapeutic Implications From A Prospective Cohort Study", Circulation Journal of the American Heart Association, 109, 2004, pp. 1004-1009.
Mullens, et al., "Elevated Intra-Abdominal Pressure In Acute Decompensated Heart Failure. A Potential Contributor To Worsening Renal Function", Journal of the American College of Cardiology, vol. 51, 2008, pp. 300-306.
Mullens, et al., "Importance Of Venous Congestion For Worsening Of Renal Function In Advanced Decompensated Heart Failure", Journal of American College of Cardiology, vol. 53, 2009, pp. 589-596.
Mullens, et al., "Prompt Reduction In Intra-Abdominal Pressure Following Large-Volume Mechanical Fluid Removal Improves Renal Insufficiency In Refractory Decompensated Heart Failure", Journal of Cardiac Failure, vol. 14, 2008, pp. 508-514.
Notarius, et al., "Central Venous Pressure During Exercise: Role Of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Schmitz-Rode, et al., "An Expandable Percutaneous Catheter Pump For Left Ventricular Support", Journal of the American College of Cardiology, vol. 45, 2005, pp. 1856-1861.
Semple, et al., "Effect Of Increased Renal Venous Pressure On Circulatory "Autoregulation" Of Isolated Dog Kidneys", Circulation Research Journal of The American Heart Association, vol. 7, 1959, pp. 643-648.
Tang, et al., "Anemia In Chronic Heart Failure: Prevalence, Etiology, Clinical Correlates, And Treatment Options", Circulation Journal of the American Heart Association, vol. 113, 2006, pp. 2454-2461.

(56) References Cited

OTHER PUBLICATIONS

Uthoff, et al., "Central Venous Pressure At Emergency Room Presentation Predicts Cardiac Rehospitalization In Patients With Decompensated Heart Failure", European Journal of Heart Failure, vol. 12, Mar. 11, 2010, 8 Pages.
Wencker, "Acute Cardio-Renal Syndrome: Progression From Congestive Heart Failure To Congestive Kidney Failure", Current Heart Failure Reports, vol. 4, 2007, pp. 134-138.
Winton, "The Control Of Glomerular Pressure By Vascular Changes Within The Mammalian Kidney, Demonstrated By The Actions Of Adrenaline", Journal of Physiology, vol. 73, Nov. 1931, pp. 151-162.
Winton, "The Influence Of Venous Pressure On The Isolated Mammalian Kidney", Journal of Physiology, vol. 72(1), Jun. 6, 1931, pp. 49-61.
Wood, "The Mechanism Of The Increased Venous Pressure With Exercise In Congestive Heart Failure", Journal of Clinical Investigation, vol. 41(11), 1962, pp. 2020-2024.
Yancy, et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, vol. 47(1), 2006, pp. 76-84.
Final Office Action for U.S. Appl. No. 15/888,771 dated Apr. 28, 2020.
Non-Final Office Action for U.S. Appl. No. 16/278,323 dated May 22, 2020.
U.S. Appl. No. 15/574,948, filed Nov. 17, 2017.
U.S. Appl. No. 16/859,100, filed Apr. 27, 2020.
U.S. Appl. No. 16/859,492, filed Apr. 27, 2020.
Corrected Notice of Allowance for U.S. Appl. No. 15/312,034 dated Feb. 12, 2020.
Issue Notification for U.S. Appl. No. 15/312,034 dated Feb. 19, 2020.
Non-Final Office Action for U.S. Appl. No. 15/574,948 dated Jan. 13, 2020.
Notice of Allowance for U.S. Appl. No. 15/312,034 dated Jan. 15, 2020.
Office Action for Chinese Application No. 201810418034.0 and dated Nov. 1, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/281,264, filed Feb. 21, 2019.
Extended European Search Report for EP Patent Application No. 19212211.7 dated Mar. 31, 2020.
Extended European Search Report for EP Patent Application No. 19215724.6 dated Apr. 1, 2020.
Extended European Search Report for EP Patent Application No. 19216488.7 dated Apr. 1, 2020.
Extended European Search Report for EP Patent Application No. 19216593.4 dated Apr. 6, 2020.
Final Office Action for U.S. Appl. No. 15/574,948, dated Aug. 26, 2020.
Non-Final Office Action for U.S. Appl. No. 16/273,898, dated Jun. 18, 2020.
Extended European Search Report for EP Patent Application No. 20179137.3 dated Oct. 9, 2020.
Final Office Action for U.S. Appl. No. 16/273,898, dated Nov. 5, 2020.
Non-Final Office Action for U.S. Appl. No. 16/281,385, dated. Oct. 14, 2020.
Non-Final Office Action for U.S. Appl. No. 16/335,786, dated. Sep. 17, 2020.
Non-Final Office Action for U.S. Appl. No. 16/345,389, dated. Oct. 26, 2020.
Notice of Allowance for U.S. Appl. No. 16/278,323, dated Oct. 29, 2020.
Office Action for Australian Application No. 2020201055 dated. Sep. 15, 2020.
Office Action for Chinese Application No. 201810418034.0 dated Aug. 4, 2020.
Office Action for Chinese Application No. 201811196500.1 dated Aug. 28, 2020.

\* cited by examiner

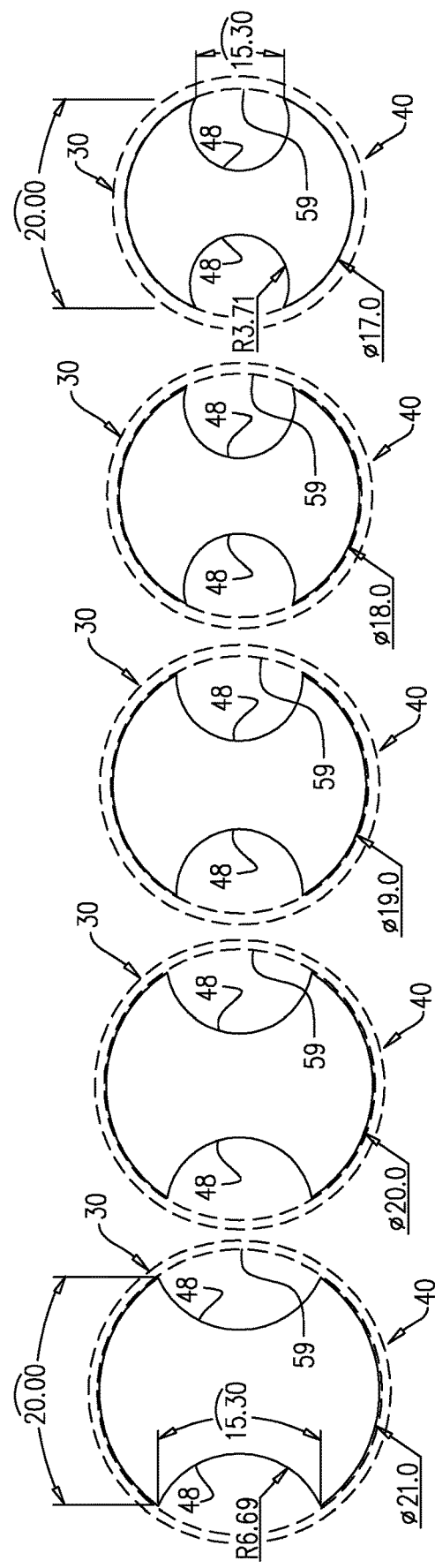

INFERIOR VENA CAVA BLOOD-FLOW IMPLANT

CROSS-REFERENCE TO RELATED APPLICATIONS

The present application claims the benefit of U.S. Provisional Application 62/649,788, filed Mar. 29, 2018, which is incorporated herein by reference.

FIELD OF THE APPLICATION

The present invention relates generally to implants.

SUMMARY OF THE APPLICATION

Embodiments of the present invention provide an inferior vena cava (IVC) implant for implantation in an IVC in a vicinity of junctions between the renal veins and the IVC. For some applications, the IVC implant is configured to treat, either on a chronic or an acute basis, cardiac dysfunction, congestive heart failure, low renal blood flow, high renal vascular resistance, arterial hypertension, and/or kidney dysfunction. The IVC implant is configured to reduce pressure in the renal veins, which typically increases perfusion of the kidney.

In some applications of the present invention, the IVC implant comprises a tubular implant body which is configured to assume a compressed delivery configuration and an expanded deployment configuration, and configured such that when implanted in the expanded deployment configuration in the IVC in the vicinity of the renal junctions, has a generally tubular shape, and has an upstream end and a downstream end.

The tubular implant body is shaped so as to define: (a) the two indentations on opposite sides of the tubular implant body (typically approximately 180 degrees apart around the tubular implant body), which are shaped so as to allow blood flow in the two indentations from upstream of the tubular implant body to downstream of the tubular implant body, and (b) one or more surfaces that at least partially block blood flow through an interior of the tubular implant body from upstream of the tubular implant body to downstream of the tubular implant body.

The tubular implant body, while in the compressed delivery configuration, is delivered to the IVC in the vicinity of the junctions between the renal veins and the IVC. The tubular implant body is transitioned to the expanded deployment configuration in which the tubular implant body has the generally tubular shape and partially blocks blood flow through the IVC and redirects the blood flow to respective IVC areas into which blood flows from the renal veins. As a result, the velocity of blood flow in the IVC areas is greater than upstream of the tubular implant body, and greater than if the IVC implant were not provided. This increased velocity of blood flow causes a reduction in blood pressure in the IVC areas, as a result of the Venturi effect, as is known in the fluid dynamics art. This reduction in blood pressure in turn causes a reduction of blood pressure in the renal veins, as mentioned above.

For some applications, when the tubular implant body is transitioned to the expanded deployment configuration, the tubular implant body partially blocks the blood flow through the IVC by touching a portion of a wall of the IVC at locations around the wall at which the renal vein junctions are not disposed. Alternatively, the tubular implant body partially blocks the blood flow through the IVC by nearly touching a portion of the wall of the IVC at locations around the wall at which the renal vein junctions are not disposed.

Typically, the tubular implant body, when implanted in the expanded deployment configuration, is shaped so as to allow approximately equal blood flow in the two indentations from upstream of the tubular implant body to downstream of the tubular implant body.

The tubular implant body may be configured to reduce the blood pressure in the IVC downstream of the tubular implant body compared to upstream of the tubular implant body in order to treat heart failure.

Typically, either immediately upon expansion or over time after implantation, the tubular implant body fills with blood, which may coagulate over time. The blood may enter through one or more upstream-facing or downstream-facing openings, such as described hereinabove, or through porosity of the wall (e.g., fabric) of the tubular implant body. Alternatively, for some applications, the tubular implant body is filled with a material other than blood during implantation.

Typically, the tubular implant body is configured such that when in the expanded deployment configuration, indentations, in cross-section, are shaped as respective smooth curves, the cross-section taken perpendicular to a central longitudinal axis of the tubular implant body. Optionally, the smooth curves are arcs. Optionally, these arcs are convex or concave. Optionally, the indentations are straight.

Alternatively or additionally, for some applications, the tubular implant body, when in the expanded deployment configuration, is shaped in cross-section so as to define two curved portions that alternate with indentations around the tubular implant body, the cross-section taken perpendicular to the central longitudinal axis of the tubular implant body at an axial location along the tubular implant body having a greatest cross-sectional area. For some applications, the two curved portions are two circular arcs.

For some applications, the tubular implant body comprises a stent frame and a fabric attached to the stent frame, either inside or outside the stent frame, or partially inside and partially outside. Optionally, the stent frame may continue along the axial length beyond the fabric either upstream and/or downstream. The stent frame may be either self-expanding, i.e., configured to automatically transition from the compressed delivery configuration to the expanded deployment configuration upon being released from the delivery catheter, e.g., comprising a superelastic alloy (such as Nitinol) having a shape memory, or balloon-expandable, e.g., comprising a plastically-deformable metal such as stainless steel, cobalt-chromium, or titanium. The fabric is biologically compatible, and may be substantially blood-impervious, or somewhat blood-impervious. For example, the fabric may comprise one or more of the following materials: a woven polyester, polyurethane, polyethylene terephthalate (PET), expanded polytetrafluoroethylene (ePTFE), and GORE-TEX® (W. L. Gore and Associates, Newark, Del., USA). For other applications, the tubular implant body comprises a single integral piece, e.g., comprising a polymer with a shape memory.

For some applications, the tubular implant body is configured such that when implanted in the expanded deployment configuration in the IVC, the one or more surfaces comprise one or more upstream-facing surfaces that face at least partially upstream, and at least partially block blood flow from upstream of the IVC into the interior of the tubular implant body. Alternatively or additionally, for some applications, the tubular implant body is configured such that when implanted in the expanded deployment configuration in the IVC, the one or more surfaces further comprise one or more downstream-facing surfaces that face at least partially downstream, and at least partially block the blood flow between the interior of the tubular implant body and downstream of the tubular implant body.

For some applications, the tubular implant body, when in the expanded deployment configuration, narrows from an upstream-most point of the two indentations toward the upstream end of the tubular implant body. Gradual widening of the upstream end in the downstream direction may reduce blood turbulence and/or head loss (pressure loss). Alternatively or additionally, for some applications, the tubular implant body, when in the expanded deployment configuration, narrows from a downstream-most point of the two indentations toward the downstream end of the tubular implant body.

These narrowing leading and trailing surfaces of the tubular implant body reduce pressure loss in the IVC that may be caused by the tubular implant body. In some applications, a certain amount of pressure loss is desirable. For some applications, the tubular implant body is configured such that when implanted in the expanded deployment configuration in the IVC, a blood pressure immediately downstream of the tubular implant body is in the normal range of 2-6 mm Hg. In other applications the pressure immediately downstream at least 70% of a blood pressure immediately upstream of the tubular implant body. Alternatively or additionally, for some applications, the pressure immediately downstream at most 50% of a blood pressure immediately upstream of the tubular implant body.

There is therefore provided, in accordance with an application of the present invention, apparatus for implantation in an inferior vena cava (IVC) in a vicinity of junctions between renal veins and the IVC, the apparatus including an IVC implant, which includes a tubular implant body, which is:

configured to assume a compressed delivery configuration and an expanded deployment configuration, and configured such that when implanted in the expanded deployment configuration in the IVC in the vicinity of the renal junctions, (a) has a generally tubular shape, (b) has upstream and downstream ends, and (c) is shaped so as to define:

two indentations on opposite sides of the tubular implant body, which are shaped so as to allow blood flow in the two indentations from upstream of the tubular implant body to downstream of the tubular implant body, and one or more surfaces that at least partially block blood flow through an interior of the tubular implant body from upstream of the tubular implant body to downstream of the tubular implant body.

For some applications, the tubular implant body is configured such that when implanted in the expanded deployment configuration in the IVC, the one or more surfaces include one or more upstream-facing surfaces that face at least partially upstream, and at least partially block blood flow from upstream of the IVC into the interior of the tubular implant body.

For some applications, the tubular implant body is configured such that when implanted in the expanded deployment configuration in the IVC, the one or more surfaces further include one or more downstream-facing surfaces that face at least partially downstream, and at least partially block the blood flow between the interior of the tubular implant body and downstream of the tubular implant body.

For some applications, the tubular implant body is configured such that when implanted in the expanded deployment configuration in the IVC, the one or more upstream-facing surfaces entirely block the blood flow from upstream of the IVC into the interior of the tubular implant body.

For some applications, the tubular implant body is configured such that when implanted in the expanded deployment configuration in the IVC, the one or more upstream-facing surfaces include exactly one upstream-facing surface.

For some applications, the tubular implant body is configured such that when implanted in the expanded deployment configuration in the IVC, the one or more upstream-facing surfaces include a plurality of upstream-facing surfaces.

For some applications, the tubular implant body, when in the expanded deployment configuration, is shaped such that the plurality of upstream-facing surfaces face partially upstream in different respective directions.

For some applications, the tubular implant body is configured such that when implanted in the expanded deployment configuration in the IVC, the one or more surfaces include one or more downstream-facing surfaces that at least partially block the blood flow between the interior of the tubular implant body and downstream of the tubular implant body.

For some applications, the tubular implant body is configured such that when implanted in the expanded deployment configuration in the IVC, the one or more downstream-facing surfaces entirely block the blood flow between the interior of the tubular implant body and downstream of the IVC.

For some applications, the tubular implant body is configured such that when implanted in the expanded deployment configuration in the IVC, the one or more downstream-facing surfaces include exactly one downstream-facing surface.

For some applications, the tubular implant body is configured such that when implanted in the expanded deployment configuration in the IVC, the one or more downstream-facing surfaces include a plurality of downstream-facing surfaces.

For some applications, the tubular implant body is configured such that when in the expanded deployment configuration, the indentations, in cross-section, are shaped as respective smooth curves, the cross-section taken perpendicular to a central longitudinal axis of the tubular implant body.

For some applications, the smooth curves are arcs.

For some applications, the tubular implant body, when in the expanded deployment configuration, is shaped in cross-section so as to define two curved portions that alternate with the indentations around the tubular implant body, the cross-section taken perpendicular to a central longitudinal axis of the tubular implant body at an axial location along the tubular implant body having a greatest cross-sectional area.

For some applications, the two curved portions are two circular arcs.

For some applications, the tubular implant body, when in the expanded deployment configuration, narrows from an upstream-most point of the two indentations toward the upstream end of the tubular implant body.

For some applications, the tubular implant body, when in the expanded deployment configuration, narrows from a downstream-most point of the two indentations toward the downstream end of the tubular implant body.

For some applications, the tubular implant body is configured such that when implanted in the expanded deployment configuration in the IVC, a blood pressure immediately downstream of the tubular implant body is at least 70% of a blood pressure immediately upstream of the tubular implant body.

For some applications, the tubular implant body is configured such that when implanted in the expanded deployment configuration in the IVC, a blood pressure immediately downstream of the tubular implant body is at most 50% of a blood pressure immediately upstream of the tubular implant body.

For some applications, the tubular implant body includes: a stent frame; and a fabric attached to the stent frame.

For some applications:

the tubular implant body, when in the expanded deployment configuration, has a greatest cross-sectional area, taken perpendicular to a central longitudinal axis of the tubular implant body, along an axial portion of the tubular implant body, the two indentations extend axially at least along the axial portion, and the axial portion has an axial length of between 3 and 11 cm.

For some applications, the tubular implant body, when in the expanded deployment configuration, has an axial length of between 3 and 20 cm.

For some applications, the tubular implant body, when in the expanded deployment configuration, other than the indentations, is shaped as two circular arcs of a circle in cross-section, the cross-section taken perpendicular to a central longitudinal axis of the tubular implant body at an axial location along the tubular implant body having a greatest cross-sectional area.

For some applications, the tubular implant body, when in the expanded deployment configuration, has a greatest cross-sectional area at the axial location along the tubular implant body, the greatest cross-sectional area equal to between 70% and 95% of the area of the circle.

For some applications, the circle has a diameter of between 1.3 and 3.5 cm.

For some applications, the tubular implant body, when implanted in the expanded deployment configuration, is shaped so as to allow approximately equal blood flow in the two indentations from upstream of the tubular implant body to downstream of the tubular implant body.

There is further provided, in accordance with an application of the present invention, a method for reducing pressure in renal veins, including:

delivering a tubular implant body of an inferior vena cava (IVC) implant, while the tubular implant body is in a compressed delivery configuration, to the IVC in a vicinity of junctions between the renal veins and the IVC; and transitioning the tubular implant body to an expanded deployment configuration in which the tubular implant body has a generally tubular shape and partially blocks blood flow through the IVC and redirects the blood flow to respective IVC areas into which blood flows from the renal veins.

For some applications, transitioning includes transitioning the tubular implant body to the expanded deployment configuration in which the tubular implant body partially blocks the blood flow through the IVC by touching a portion of a wall of the IVC at locations around the wall at which the renal junctions are not disposed.

For some applications, the tubular implant body, when in the expanded deployment configuration, is not circular in cross-section at any axial location along the tubular implant body having a greatest cross-sectional area, the cross-section taken perpendicular to a central longitudinal axis of tubular implant body.

For some applications, the tubular implant body, when in the expanded deployment configuration, is generally circular in cross-section, the cross-section taken perpendicular to a central longitudinal axis of tubular implant body at an axial location along the tubular implant body having a greatest cross-sectional area.

For some applications, transitioning includes transitioning the tubular implant body to the expanded deployment configuration in which the tubular implant body, at an axial location along the tubular implant body having a greatest cross-sectional area, blocks all but between 5% and 30% of an original cross-sectional area of the IVC at the axial location along the tubular implant body, the original cross-sectional area prior to delivering the tubular implant body to the IVC, and the cross-sections taken perpendicular to a central longitudinal axis of the tubular implant body.

For some applications, transitioning includes transitioning the tubular implant body to the expanded deployment configuration in which the tubular implant body, at the axial location, blocks all but between 10% and 30% of the original cross-sectional area of the IVC.

For some applications, transitioning includes transitioning the tubular implant body to the expanded deployment configuration in which the tubular implant body, at the axial location, blocks all but between 15% and 30% of the original cross-sectional area of the IVC.

For some applications, transitioning includes transitioning the tubular implant body to the expanded deployment configuration in which the tubular implant body, at the axial location, blocks all but between 25% and 30% of the original cross-sectional area of the IVC.

For some applications, transitioning includes transitioning the tubular implant body to the expanded deployment configuration in which the blood flow to the respective IVC areas is approximately equal.

For some applications, the method further includes, after transitioning the tubular implant body to an expanded deployment configuration, adjusting a degree to which the tubular implant body partially blocks the blood flow through the IVC.

For some applications, the method further includes, after transitioning the tubular implant body to the expanded deployment configuration, adjusting a degree to which the tubular implant body causes pressure loss downstream of the IVC implant.

The present invention will be more fully understood from the following detailed description of embodiments thereof, taken together with the drawings, in which:

BRIEF DESCRIPTION OF THE DRAWINGS

FIGS. 7A-E are cross-sectional schematic views of several configurations of a single IVC implant of FIGS. 1-5C, in accordance with an application of the present invention.

The present invention will be more understood from the following detailed description of embodiments thereof, taken together with the drawings, in which:

DETAILED DESCRIPTION OF APPLICATIONS

Figure 1:
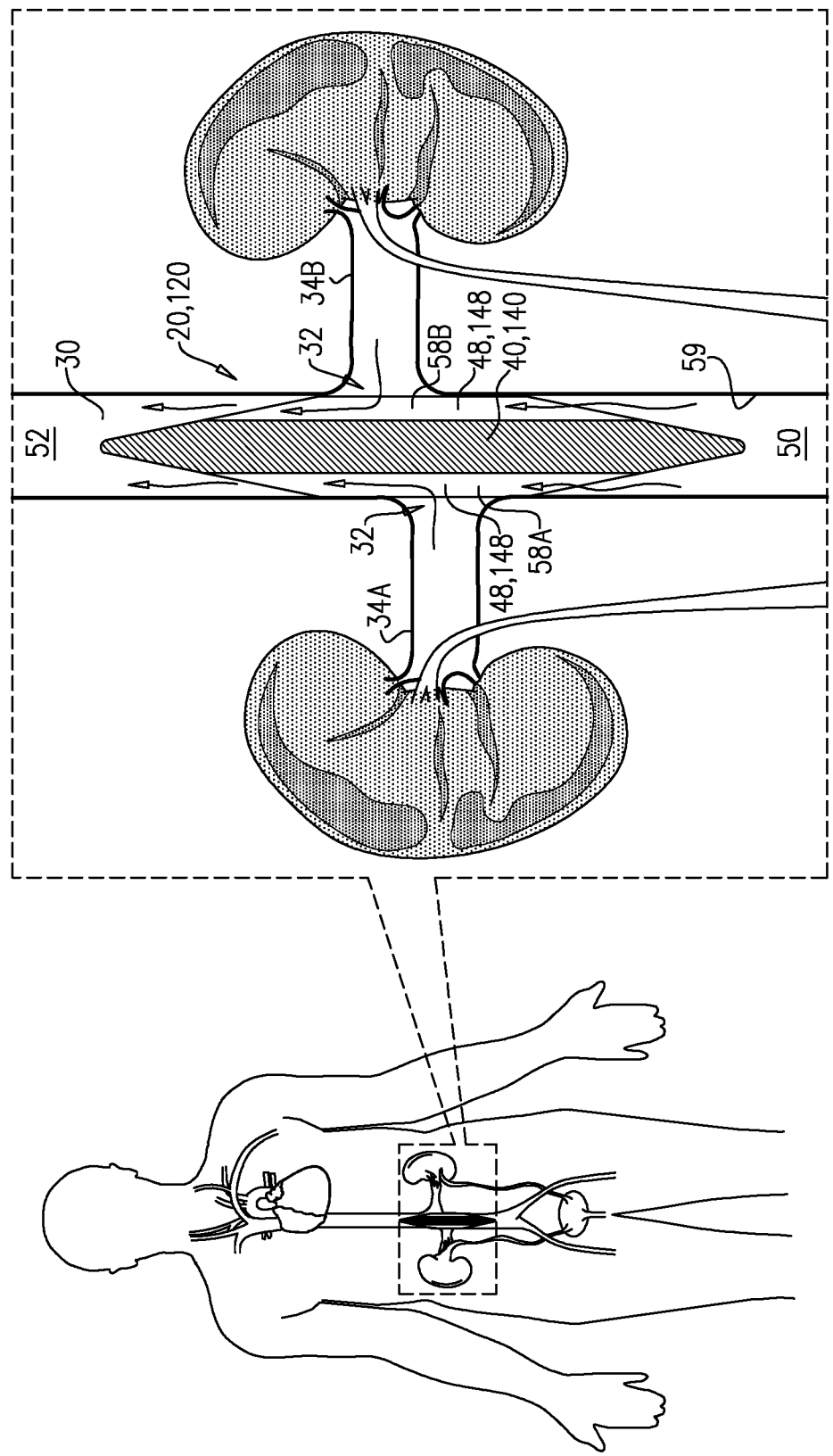
FIG. 1 is a schematic illustration of an inferior vena cava (IVC) implant implanted in an IVC in a vicinity of junctions between renal veins and the IVC, in accordance with an application of the present invention.

FIG. 1 is a schematic illustration of an inferior vena cava (IVC) implant 20 implanted in an IVC 30 in a vicinity of junctions 32 between renal veins 34A and 34B and IVC 30, in accordance with an application of the present invention. For some applications, IVC implant 20 is configured to treat, either on a chronic or an acute basis, cardiac dysfunction, congestive heart failure, low renal blood flow, high renal vascular resistance, arterial hypertension, and/or kidney dysfunction. IVC implant 20 is configured to reduce pressure in renal veins 34A and 34B, which typically increases perfusion of the kidney. IVC implant 20 comprises a tubular implant body 40.

Figure 2A:
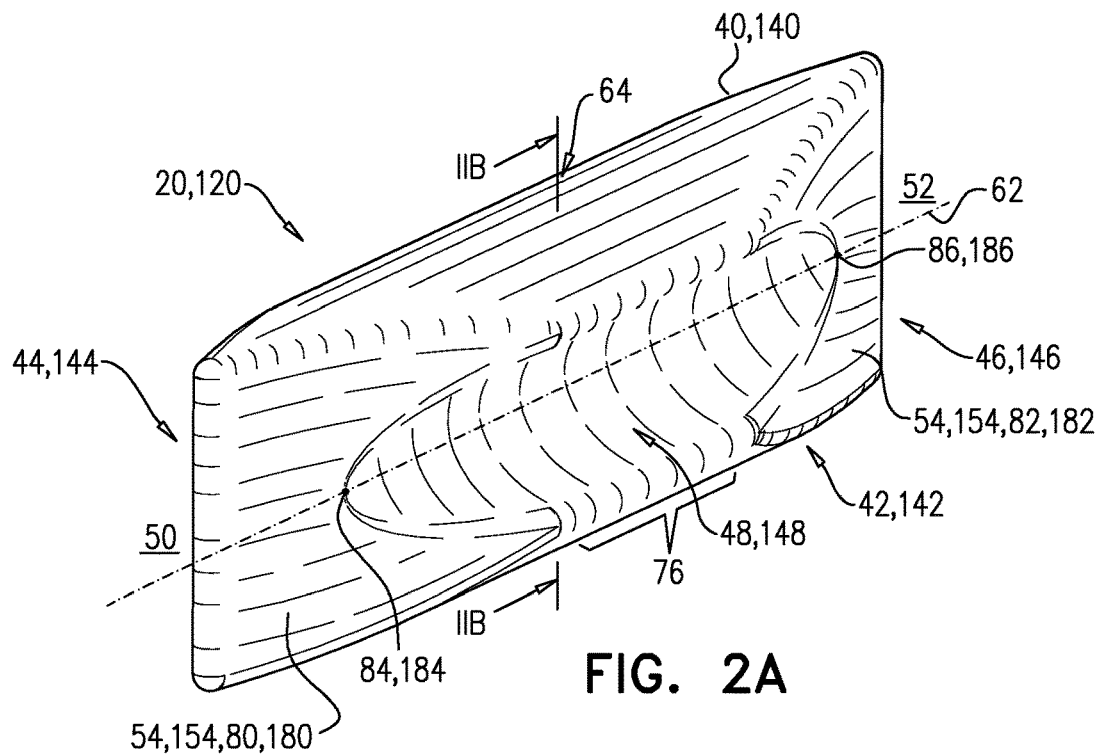
FIG. 2A-B are schematic illustrations of an IVC implant, in accordance with an application of the present invention.
Figure 2B:
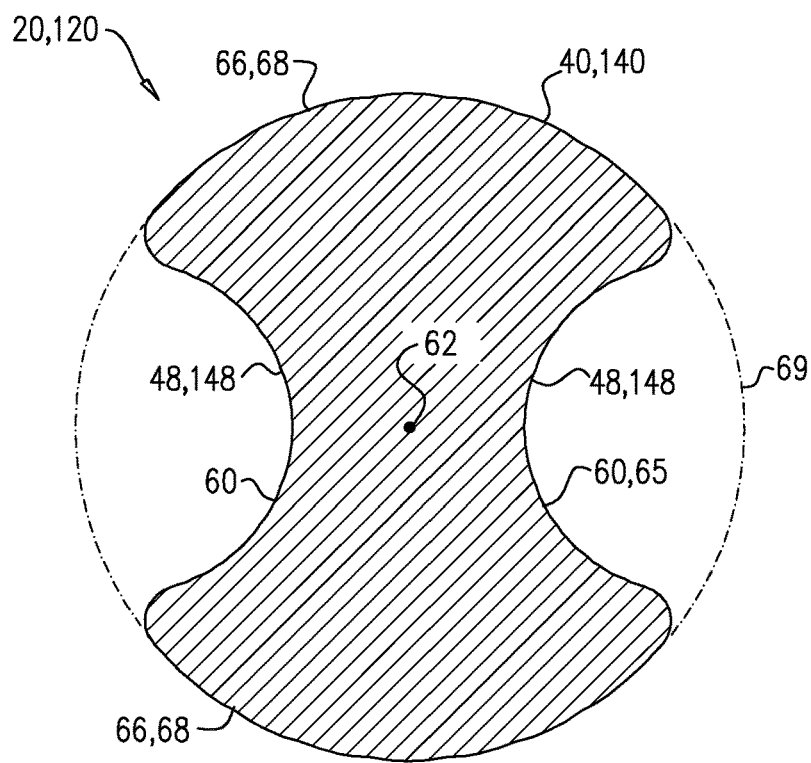

Reference is still made to FIG. 1, and is additionally made to FIG. 2A-B, which are schematic illustrations of an IVC implant 120, in accordance with an application of the present invention. IVC implant 120 is one configuration of IVC implant 20. FIG. 1 also shows this configuration of IVC implant 20. FIG. 2B is a cross-sectional view of IVC implant 120, taken along line IIB-IIB.

IVC implant 20, 120 comprises a tubular implant body 40, 140, which is:
- configured to assume a compressed delivery configuration and an expanded deployment configuration (tubular implant body 40, 140 is shown in the expanded deployment configuration in all of the figures), and
- configured such that when implanted in the expanded deployment configuration in IVC 30 in the vicinity of renal junctions 32, tubular implant body 40, 140 has a generally tubular shape 42, 142, and has an upstream end 44, 144 and a downstream end 46, 146.

Tubular implant body 40, 140 is shaped so as to define:
- two indentations 48, 148 on opposite sides of tubular implant body 40, 140 (typically approximately 180 degrees apart around tubular implant body 40, 140), which are shaped so as to allow blood flow in the two indentations 48, 148 from upstream 50 of tubular implant body 40, 140 to downstream 52 of tubular implant body 40, 140, and
- one or more surfaces 54, 154 that at least partially block blood flow through an interior of tubular implant body 40, 140 from upstream 50 of tubular implant body 40, 140 to downstream 52 of tubular implant body 40, 140.

As used in the present application, including in the claims, a "generally tubular shape" means generally having the form of a tube, i.e., a hollow elongated structure; one or both of ends of the tube may be open, closed, and/or partially open and closed, as is known in the tube manufacturing art. As described herein, the shape and cross-sectional area of the tube may vary therealong or may be constant.

More generally, for some applications, tubular implant body 40, 140, when in the expanded deployment configuration, is not circular in cross-section at any axial location along tubular implant body 40, 140 having a greatest cross-sectional area, the cross-section taken perpendicular to a central longitudinal axis 62 of tubular implant body 40, 140.

Reference is again made to FIG. 1. Tubular implant body 40, 140, while in the compressed delivery configuration, is delivered to IVC 30 in the vicinity of junctions 32 between renal veins 34A and 34B and IVC 30. Tubular implant body 40, 140 is transitioned to the expanded deployment configuration in which tubular implant body 40, 140 has generally tubular shape 42, 142 and partially blocks blood flow through IVC 30 and redirects the blood flow to respective IVC areas 58A and 58B into which blood flows from renal veins 34A and 34B. As a result, the velocity of blood flow in IVC areas 58A and 58B is greater than upstream 50 of tubular implant body 40, 140, and greater than if IVC implant 20 were not provided. This increased velocity of blood flow causes a reduction in blood pressure in IVC areas 58A and 58B, as a result of the Venturi effect, as is known in the fluid dynamics art. This reduction in blood pressure in turn causes a reduction of blood pressure in renal veins 34A and 34B, as mentioned above.

For some applications, when tubular implant body 40, 140 is transitioned to the expanded deployment configuration, tubular implant body 40, 140 partially blocks the blood flow through IVC 30 by touching a portion of a wall 59 of IVC 30 at locations around wall 59 at which renal junctions 32 are not disposed. Alternatively, tubular implant body 40, 140 partially blocks the blood flow through IVC 30 by nearly touching a portion of wall 59 of IVC 30 at locations around wall 59 at which renal junctions 32 are not disposed.

Typically, tubular implant body 40, 140, when implanted in the expanded deployment configuration, is shaped so as to allow approximately equal blood flow in the two indentations 48, 148 from upstream 50 of tubular implant body 40, 140 to downstream 52 of tubular implant body 40, 140.

Tubular implant body 40, 140 may be configured to reduce the blood pressure in IVC 30 downstream 52 of tubular implant body 40, 140 compared to upstream 50 of tubular implant body 40, 140 in order to treat heart failure.

For some applications, tubular implant body 40, 140, when transitioned to the expanded deployment configuration, at an axial location 64 along tubular implant body 40, 140 having a greatest cross-sectional area, blocks all but between 5% (e.g., 7%) and 30% of an original cross-sectional area of IVC 30 at axial location 64 along tubular implant body 40, 140, the original cross-sectional area prior to delivering tubular implant body 40, 140 to IVC 30, and the cross-sections taken perpendicular to central longitudinal axis 62 of tubular implant body 40, 140. For example, tubular implant body 40, 140, at axial location 64, may block all but between 5% (e.g., 7%) and 10%, all but between 10% and 30% (e.g., all but between 10% and 15%), all but between 15% and 30% (e.g., all but between 15% and 25%), or all but between 25% and 30% of the original cross-sectional area of IVC 30. Optionally, the total range of non-IVC-blockage of 5% (e.g., 7%) and 30% can be broken down as follows based on the values in Table I below: for IVC pressures between 5-30%, in order to reduce the downstream pressure to zero, the non-IVC-blockage range is 7-18%. In order to reduce the downstream pressure to half of the upstream pressure, the non-IVC-blockage range is 10-25%. In order to reduce the downstream pressure to ⅔ of the upstream pressure, the non-IVC-blockage range is 13-30%. For example, if the upstream pressure is 10-20, in order to reduce the downstream pressure to: zero, the non-IVC-blockage range is 9-13%; to half, the non-IVC-blockage range is 13-18%; and to ⅔, the non-IVC-blockage range is 16-22%. All the above discussion is true for specific velocity, viscosity, etc.

Alternatively, for some applications, tubular implant body 40, 140, when transitioned to the expanded deployment configuration, at the above-mentioned axial location 64 along tubular implant body 40, 140 having the greatest cross-sectional area, blocks all but between 30% and 80% of the original cross-sectional area of IVC 30 at axial location 64 along tubular implant body 40, 140. This non-IVC-blockage range may be appropriate, for example, for allowing exercise, during which the velocity of blood may be significantly higher.

Typically, either immediately upon expansion or over time after implantation, tubular implant body 40, 140 fills with blood, which may coagulate over time. The blood may enter through one or more upstream-facing or downstream-facing openings, such as described hereinabove, or through porosity of the wall (e.g., fabric) of the tubular implant body. Alternatively, for some applications, the tubular implant body is filled with a material other than blood during implantation.

It is noted that in many of the configurations of tubular implant body 40, including those shown in FIGS. 1-5B, the tubular implant body has the greatest cross-sectional area at a plurality of contiguous locations along the tubular implant body, rather than at exactly one location along the tubular implant body.

Reference is again made to FIGS. 2A-B. Typically, tubular implant body 40, 140 is configured such that when in the expanded deployment configuration, indentations 48, 148, in cross-section, are shaped as respective smooth curves 60, the cross-section taken perpendicular to central longitudinal axis 62 of tubular implant body 40, 140. Optionally, smooth curves 60 are arcs 65. Optionally, these arcs are convex or concave. Optionally, the indentations are straight.

Alternatively or additionally, for some applications, tubular implant body 40, 140, when in the expanded deployment configuration, is shaped in cross-section so as to define two curved portions 66 that alternate with indentations 48, 148 around tubular implant body 40, 140, the cross-section taken perpendicular to central longitudinal axis 62 of tubular implant body 40, 140 at axial location 64 along tubular implant body 40, 140 having a greatest cross-sectional area. For some applications, the two curved portions 66 are two circular arcs 68, such as shown. For some applications, when tubular implant body 40, 140 is in the expanded deployment configuration, the greatest cross-sectional area at axial location 64 equals to between 70% and 95% of the area of a circle 69 defined by the two circular arcs 68. For some applications, circle 69 has a diameter of between 1.3 and 3.5 cm.

For some applications, as labeled in FIG. 3A, described hereinbelow, tubular implant body 40, 140 comprises a stent frame 70 and a fabric 72 attached to stent frame 70, either inside or outside stent frame 70, or partially inside and partially outside. Optionally, stent frame 70 may continue along the axial length beyond fabric 72 either upstream and/or downstream. Stent frame 70 may be either self-expanding, i.e., configured to automatically transition from the compressed delivery configuration to the expanded deployment configuration upon being released from the delivery catheter, e.g., comprising a superelastic alloy (such as Nitinol) having a shape memory, or balloon-expandable, e.g., comprising a plastically-deformable metal such as stainless steel, cobalt-chromium, or titanium. Fabric 72 is biologically compatible, and may be substantially blood-impervious, or somewhat blood-impervious. Fabric 72 may comprise, for example, a polymeric material (e.g., a polyester, or polytetrafluoroethylene (PTFE)), a textile material (e.g., polyethylene terephthalate (PET), e.g., Dacron®, manufactured by E. I. du Pont de Nemours and Company, Wilmington, Del., USA), or expanded polytetrafluoroethylene (ePTFE), e.g., manufactured by W. L. Gore & Associates, Newark, Del., USA) or woven polyester, natural tissue (e.g., pericardium, saphenous vein or collagen), or a combination thereof.

In these applications, the tubular outline as shown in the figures is defined by fabric 72 of the wall. Stent frame 70 may have the same shape as fabric 72. Alternatively, stent frame 70 may not be contiguous with fabric 72 entirely around the perimeter. For example, stent frame 70 may be circular and only contiguous with fabric 72 in curved portions 66 and not in indentations 48, 148.

For other applications, tubular implant body 40, 140 comprises a single integral piece, e.g., comprising a polymer with a shape memory.

For some applications, tubular implant body 40, 140, when in the expanded deployment configuration, has an axial length of between 3 and 20 cm, e.g., between 6 and 11 cm.

For some applications, tubular implant body 40, 140, when in the expanded deployment configuration, has a greatest cross-sectional area, taken perpendicular to central longitudinal axis 62 of tubular implant body 40, 140, along an axial portion 76 of tubular implant body 40. The two indentations 48, 148 extend axially at least along axial portion 76. Typically, axial portion 76 has an axial length of at least 3 cm, no more than 11 cm, and/or between 3 and 8 cm. In some configurations, tapered shape remnants of indentations 48, 148 continue nearly to one or both of upstream end 44, 144 and downstream end 46, 146, such as when one or both of the ends are tapered, such as described hereinbelow.

For some applications, tubular implant body 40, 140 is configured such that when implanted in the expanded deployment configuration in IVC 30, the one or more surfaces 54, 154 comprise one or more upstream-facing surfaces 80, 180 that face at least partially upstream, and at least partially block blood flow from upstream 50 of IVC 30 into the interior of tubular implant body 40, 140. As used in the present application, including in the claims, a surface "faces partially" in a direction if the surface includes at least one vector component that faces in the direction; in other words, the surface need not face entirely in the direction in order to be considered facing at least partially in the direction. For some of these applications, such as shown in FIGS. 1 and 2A, tubular implant body 40, 140 is configured such that when implanted in the expanded deployment configuration in IVC 30, the one or more upstream-facing surfaces 80, 180 entirely block the blood flow from upstream 50 of IVC 30 into the interior of tubular implant body 40 (i.e., upstream end 44, 144 of tubular implant body 40, 140 is closed).

Alternatively or additionally, for some applications, tubular implant body 40, 140 is configured such that when implanted in the expanded deployment configuration in IVC 30, the one or more surfaces 54, 154 further comprise one or more downstream-facing surfaces 82, 182 that face at least partially downstream, and at least partially block the blood flow between the interior of tubular implant body 40, 140 and downstream 52 of tubular implant body 40, 140. For some of these applications, such as shown in FIGS. 1 and 2A, tubular implant body 40, 140 is configured such that when implanted in the expanded deployment configuration in IVC 30, the one or more downstream-facing surfaces 82, 182 entirely block the blood flow between the interior of tubular implant body 40, 140 and downstream 52 of IVC 30 (i.e., downstream end 46, 146 of tubular implant body 40, 140 is closed).

For some applications, such as shown in FIGS. 1 and 2A (and FIG. 3A, described hereinbelow), tubular implant body 40, 140 is configured such that when implanted in the expanded deployment configuration in IVC 30, the one or more upstream-facing surfaces 80, 180 comprise a plurality of upstream-facing surfaces 80, 180. Typically, tubular implant body 40, 140, when in the expanded deployment configuration, is shaped such that the plurality of upstream-facing surfaces 80, 180 face partially upstream 50 in different respective directions.

Alternatively or additionally, for some applications, such as shown in FIGS. 1 and 2A, tubular implant body 40 is configured such that when implanted in the expanded deployment configuration in IVC 30, the one or more downstream-facing surfaces 82, 182 comprise a plurality of downstream-facing surfaces 82, 182. Typically, tubular implant body 40, 140, when in the expanded deployment configuration, is shaped such that the plurality of downstream-facing surfaces 82, 182 face partially downstream 52 in different respective directions.

For some applications, such as shown in FIGS. 1-5C, tubular implant body 40, 140, when in the expanded deployment configuration, narrows from an upstream-most point 84, 184 of the two indentations 48, 148 toward upstream end 44, 144 of tubular implant body 40, 140. In other words, the one or more upstream-facing surfaces 80, 280 are tapered. Gradual widening of upstream end 44, 144 in the downstream direction may reduce blood turbulence and/or head loss (pressure loss).

Alternatively or additionally, for some applications, such as shown in FIGS. 1 and 2A, tubular implant body 40, 140, when in the expanded deployment configuration, narrows from a downstream-most point 86, 186 of the two indentations 48, 148 toward downstream end 46, 146 of tubular implant body 40, 140. In other words, the one or more downstream-facing surfaces 82, 182 are tapered.

These narrowing leading and trailing surfaces of tubular implant body 40, 140 reduce pressure loss in IVC 30 that may be caused by tubular implant body 40, 140. In some applications, a certain amount of pressure loss is desirable. For some applications, tubular implant body 40, 140 is configured such that when implanted in the expanded deployment configuration in IVC 30, a blood pressure immediately downstream 52 of tubular implant body 40, 140 is in the normal range of 2-6 mm Hg. In other applications the pressure immediately downstream at least 70% of a blood pressure immediately upstream 50 of tubular implant body 40, 140. Alternatively or additionally, for some applications, the pressure immediately downstream at most 50% of a blood pressure immediately upstream 50 of tubular implant body 40, 140.

Figure 3A:
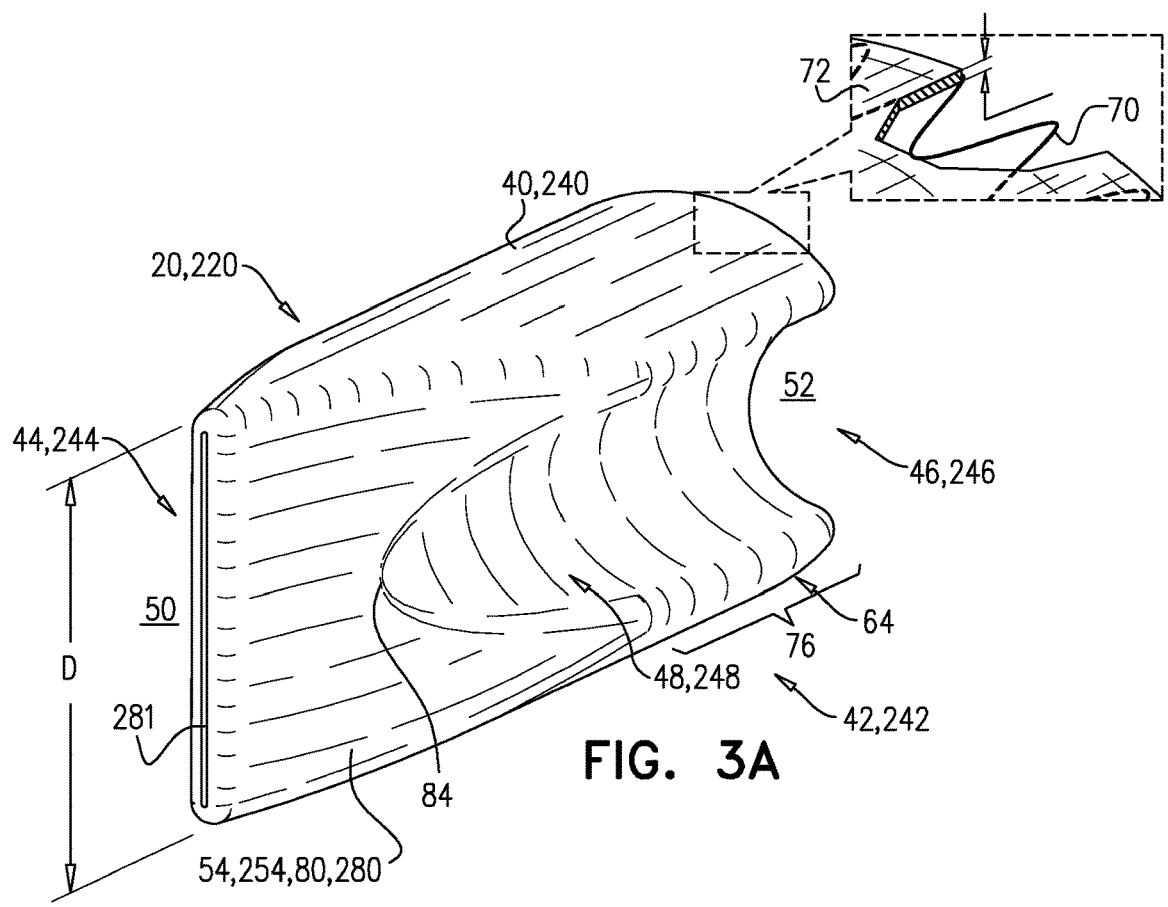
FIGS. 3A-B are schematic illustrations of another IVC implant, in accordance with an application of the present invention.
Figure 3B:
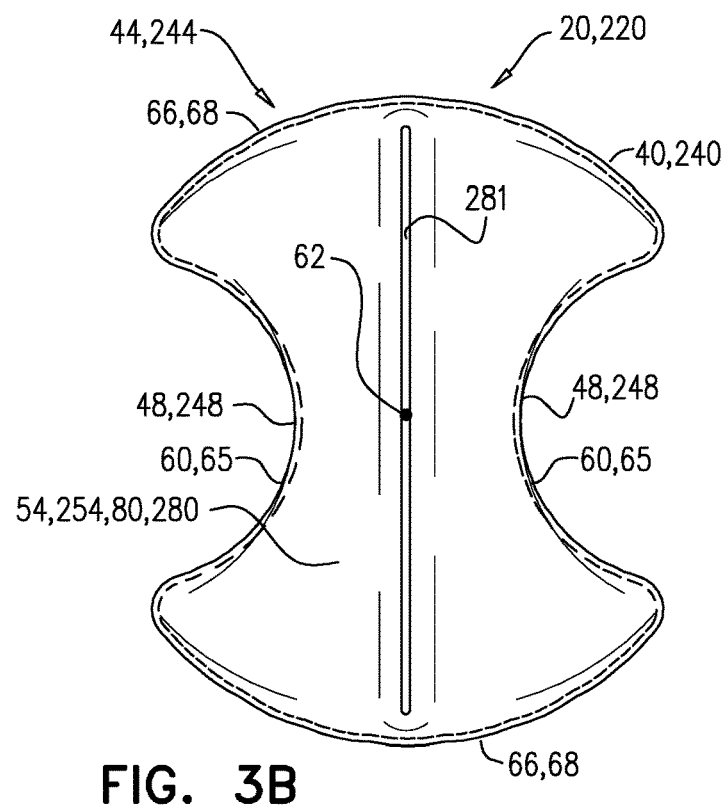

Reference is now made to FIGS. 3A-B, which are schematic illustrations of an IVC implant 20, 220, in accordance with an application of the present invention. FIG. 3B is a view from upstream end 44, 244 of a tubular implant body 40, 240 of IVC implant 20, 220. IVC implant 220 is one configuration of IVC implant 20. Except as described below, IVC implant 220 may implement any of the features of IVC implant 120, described hereinabove with reference to FIGS. 1-2B.

Tubular implant body 40, 240 is shaped so as to define two indentations 48, 248, and one or more surfaces 54, 254 that at least partially block blood flow through an interior of tubular implant body 40, 240 from upstream 50 of tubular implant body 40, 240 to downstream 52 of tubular implant body 40, 240. Tubular implant body 40, 240 is configured such that when implanted in the expanded deployment configuration in IVC 30 in the vicinity of renal junctions 32, tubular implant body 40, 240 has a generally tubular shape 42, 242, and has an upstream end 44, 244 and a downstream end 46, 246.

Tubular implant body 40, 240 of IVC implant 220 is configured such that when implanted in the expanded deployment configuration in IVC 30, one or more upstream-facing surfaces 80, 280 of tubular implant body 40, 240 only partially block the blood flow from upstream 50 of IVC 30 into the interior of tubular implant body 40, 240. In other words, upstream end 44, 244 of tubular implant body 40, 240 is partially open and thus defines at least one upstream opening 281, such as a slit, as shown in FIGS. 3A-B. For some applications, upstream opening 281 has a greatest dimension D (e.g., a length of the slit) of between 1 and 3 cm when tubular implant body 40, 280 is in the expanded deployment configuration.

Although not shown, this partially open configuration may also be implemented for downstream-facing surface 82 of the tubular implant body.

Optionally, as shown in FIG. 3A, downstream end 46, 246 of tubular implant body 40, 240, is open, i.e., is not shaped so as to define any downstream-facing surfaces.

Figure 4A:
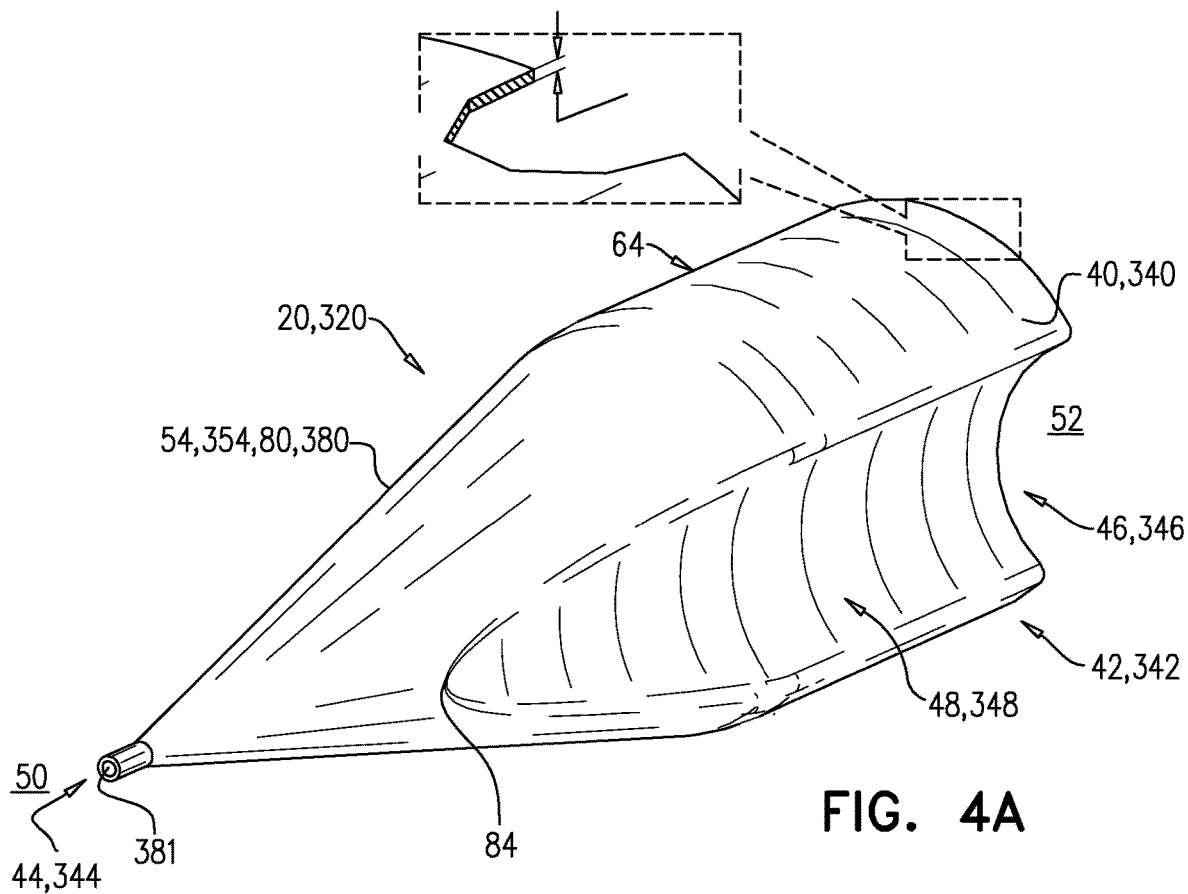
FIGS. 4A-B are schematic illustrations of yet another IVC implant, in accordance with an application of the present invention.
Figure 4B:
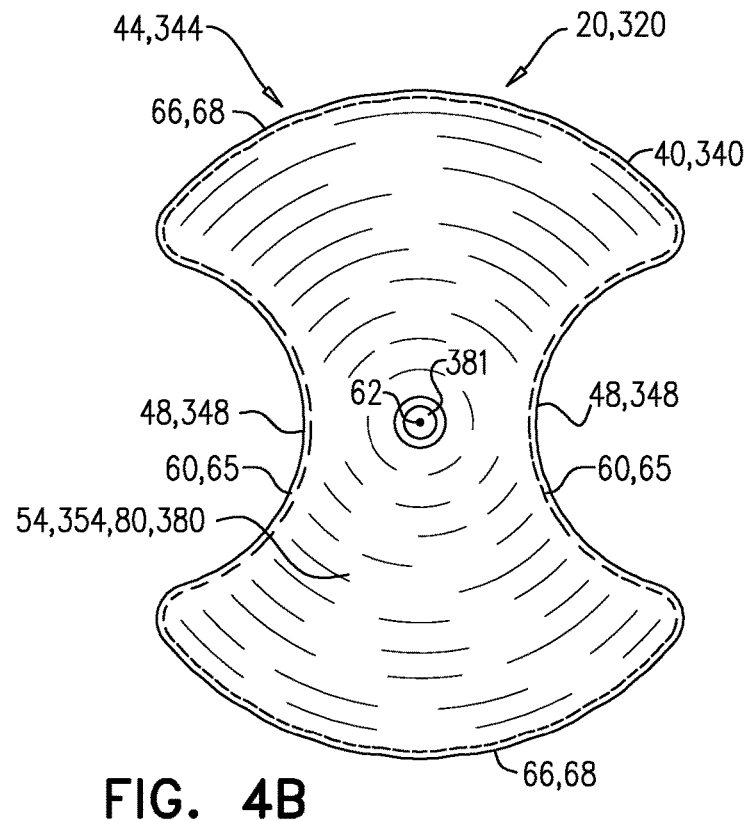

Reference is now made to FIGS. 4A-B, which are schematic illustrations of an IVC implant 20, 320, in accordance with an application of the present invention. FIG. 4B is a view from an upstream end 44, 344 of a tubular implant body 40, 340 of IVC implant 20, 320. IVC implant 320 is one configuration of IVC implant 20. Except as described below, IVC implant 320 may implement any of the features of IVC implant 120, described hereinabove with reference to FIGS. 1-2B. Also, except as described below, IVC implant 320 is generally similar to IVC implant 220, described hereinabove with reference to FIGS. 3A-B.

Tubular implant body 40, 340 is shaped so as to define two indentations 48, 348, and one or more surfaces 54, 354 that at least partially block blood flow through an interior of tubular implant body 40, 340 from upstream 50 of tubular implant body 40, 340 to downstream 52 of tubular implant body 40, 340. Tubular implant body 40, 340 is configured such that when implanted in the expanded deployment configuration in IVC 30 in the vicinity of renal junctions 32, tubular implant body 40, 340 has a generally tubular shape 42, 342, and has an upstream end 44, 344 and a downstream end 46, 346.

Tubular implant body 40, 340 is configured such that when implanted in the expanded deployment configuration in IVC 30, one or more upstream-facing surfaces 80, 380 of tubular implant body 40, 340 comprise exactly one upstream-facing surface 380. For some applications, the exactly one upstream-facing surface 380 is frustoconical, as shown, or conical (configuration not shown).

For some applications, such as shown in FIGS. 4A-B, tubular implant body 40, 340 of IVC implant 320 is configured such that when implanted in the expanded deployment configuration in IVC 30, the exactly one upstream-facing surfaces 80, 380 only partially blocks the blood flow from upstream 50 of IVC 30 into the interior of tubular implant body 40, 340. In other words, upstream end 44, 344 of tubular implant body 40, 340 is partially open and thus defines at least one upstream opening 381, such as a round hole, as shown in FIGS. 4A-B.

Although not shown, this partially open configuration may also be implemented for downstream-facing surface 82 of the tubular implant body. In addition, although not shown, tubular implant body 40, 340 may be configured such that when implanted in the expanded deployment configuration in IVC 30, tubular implant body 340 is shaped so as to define exactly one downstream-facing surfaces 82, for example, shaped like the exactly one upstream-facing surface 380.

Optionally, as shown in FIG. 4A, a downstream end 46, 246 of tubular implant body 40, 240, is open, i.e., is not shaped so as to define any downstream-facing surfaces.

Figure 5A:
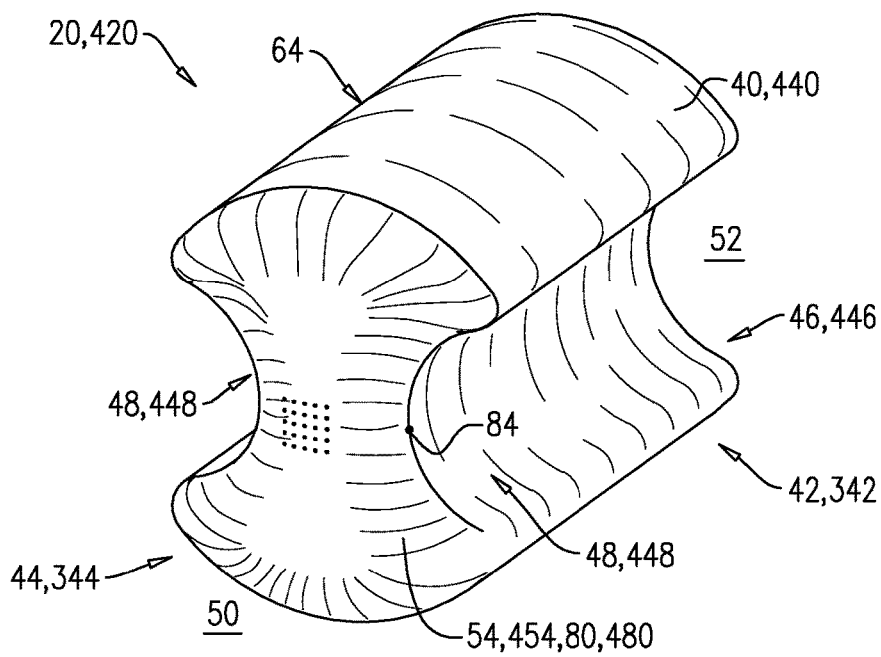
FIGS. 5A-C are schematic illustrations of still another IVC implant, in accordance with an application of the present invention.
Figure 5B:
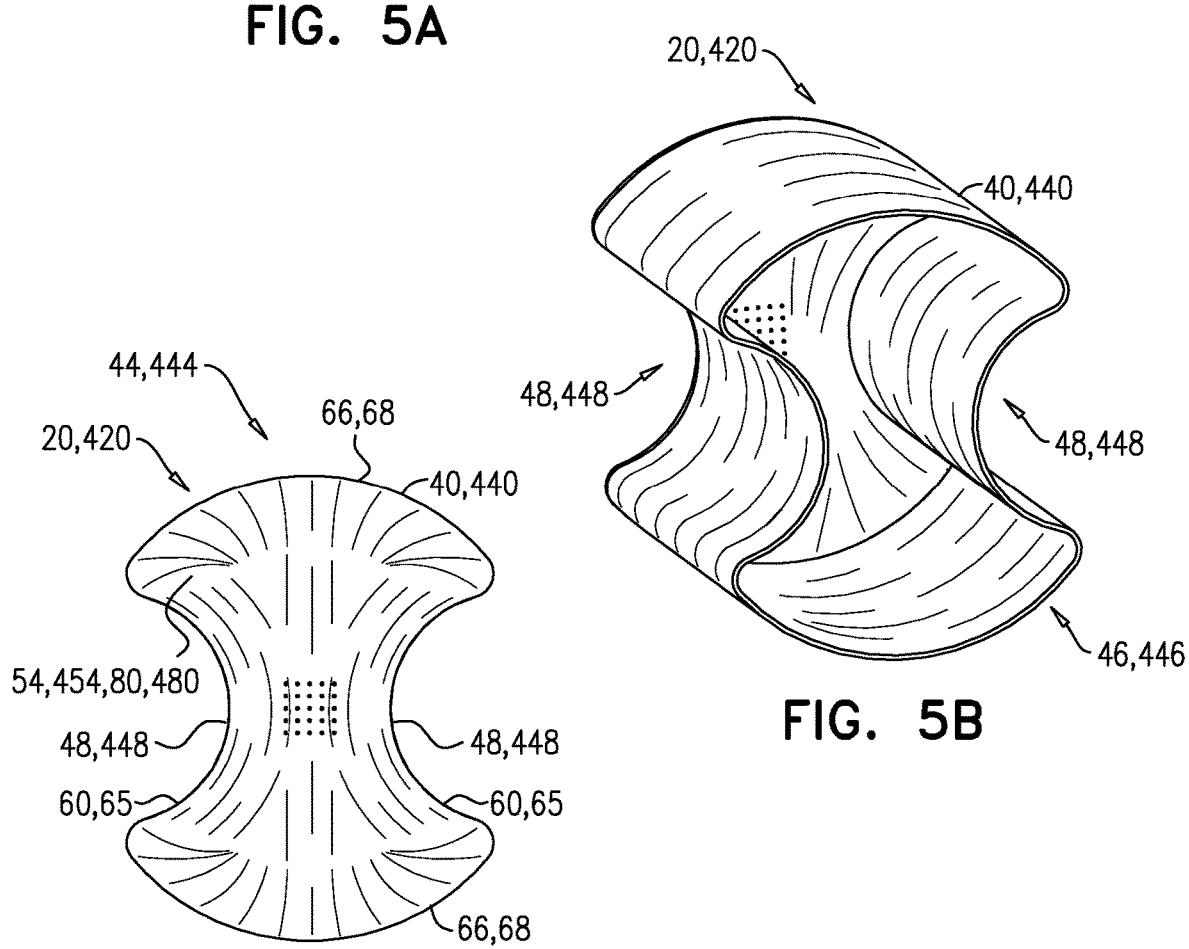
Figure 5C:
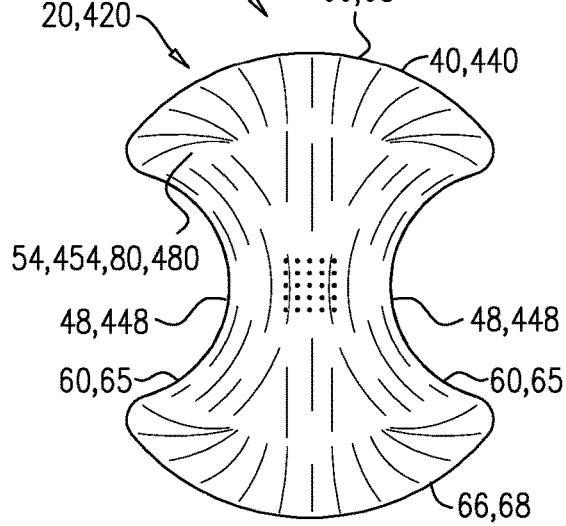

Reference is now made to FIGS. 5A-C, which are schematic illustrations of an IVC implant 20, 420, in accordance with an application of the present invention. FIGS. 5B and 5C are views from an upstream end 44, 444 and a downstream end 46, 446, respectively, of a tubular implant body 40, 440 of IVC implant 20, 420. IVC implant 420 is one configuration of IVC implant 20. Except as described below, IVC implant 420 may implement any of the features of IVC implant 120, described hereinabove with reference to FIGS. 1-2B.

Tubular implant body 40, 440 is shaped so as to define two indentations 48, 448, and one or more surfaces 54, 454 that at least partially block blood flow through an interior of tubular implant body 40, 440 from upstream 50 of tubular implant body 40, 440 to downstream 52 of tubular implant body 40, 440. Tubular implant body 40, 440 is configured such that when implanted in the expanded deployment configuration in IVC 30 in the vicinity of renal junctions 32, tubular implant body 40, 440 has a generally tubular shape 42, 442, and has an upstream end 44, 444 and a downstream end 46, 446.

As can be seen in FIGS. 5A-C, one or more upstream-facing surfaces 80, 480 may have a relatively flat profile compared to the one or more upstream-facing surface 80 in the other illustrated configurations.

Figure 6:
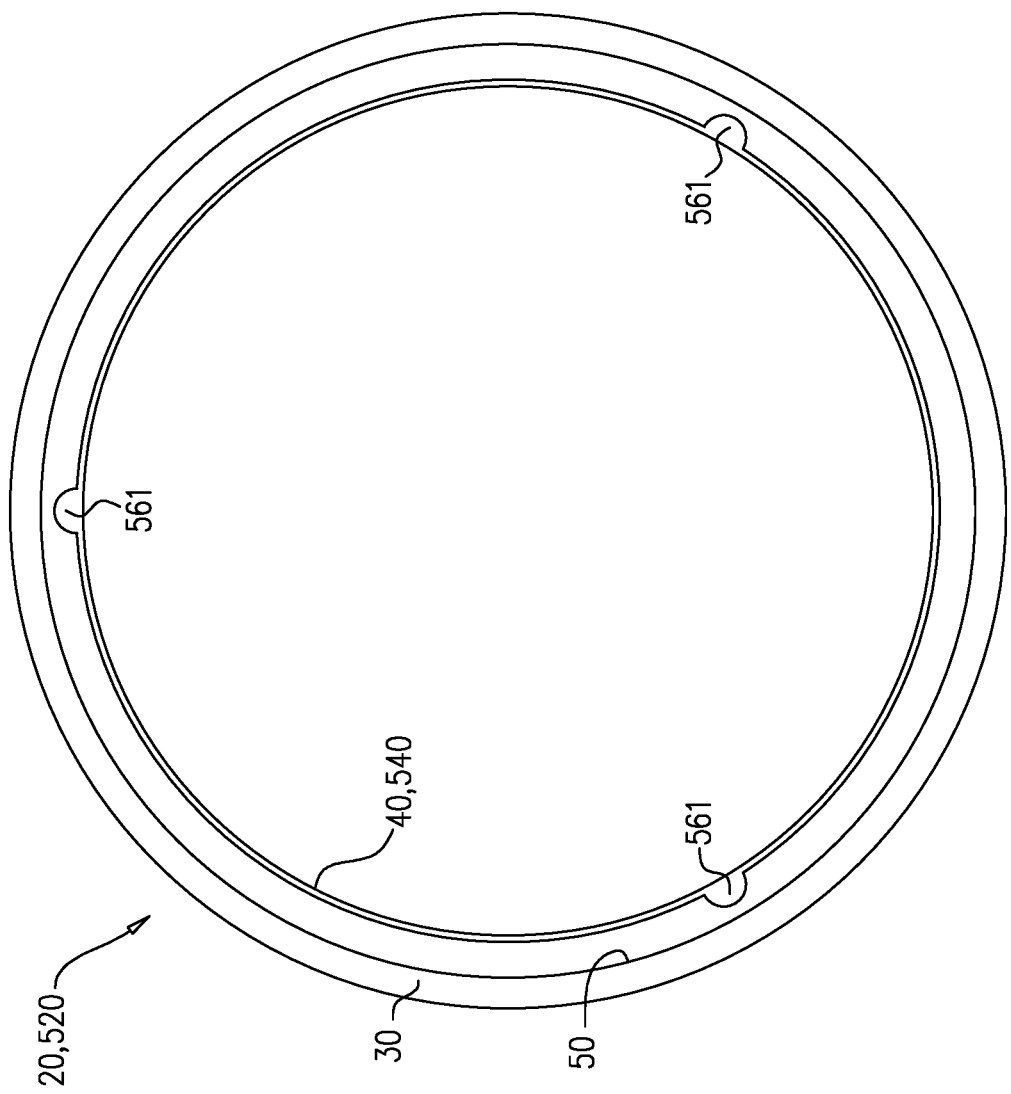
FIG. 6 is a schematic illustration of another IVC implant, in accordance with an application of the present invention.

Reference is made to FIG. 6, which is a schematic illustration of an IVC implant 20, 520, in accordance with an application of the present invention. IVC implant 520 is one configuration of IVC implant 20. Except as described below, IVC implant 520 may implement any of the features of IVC implant 20 described hereinabove with reference to FIGS. 1-5C. A tubular implant body 40, 540 of IVC implant 520 provides a round blockage placed inside IVC 30. For example, tubular implant body 40, 540 may be anchored to wall 59 of IVC 30 at three circumferential points 561, as shown, or more or fewer circumferential points (configurations not shown), by anchoring elements of IVC implant 520. Alternatively, tubular implant body 40, 540 (e.g., stent frame 70 thereof) may be anchored independently of fabric 72 at any point before during or after the central blockage.

In this configuration, tubular implant body 40, 540, when in the expanded deployment configuration, is generally circular in cross-section, the cross-section taken perpendicular to central longitudinal axis 62 of tubular implant body 40, 540 at an axial location along tubular implant body 40 having a greatest cross-sectional area.

Reference is now made to FIGS. 7A-E, which are cross-sectional schematic views of several configurations of a single IVC implant 20, in accordance with an application of the present invention. All of these cross-sections are taken perpendicular to central longitudinal axis 62 of tubular implant body 40 at axial location 64 along tubular implant body 40 having a greatest cross-sectional area. The measurements provided in FIGS. 7A-E are by way of illustration and not limitation, and the principles of this application of the present invention are equally applicable to other measurements. This application of the present invention may be implemented in combination with any of the configurations of tubular implant body 40 described hereinabove with reference to FIGS. 1-5C.

This application of the present invention allows a single IVC implant 20, having a fixed perimeter, to effectively be deployed in one or more IVCs having different diameters. This accommodation may be helpful, for example, because (a) the diameter of the IVC varies between different patients, (b) the diameter of a given patient's IVC may be incorrectly estimated because of measurement errors, and/or (c) the diameter of a given patient's IVC may change upon implantation of IVC implant 20. The cross-sectional views of FIGS. 7A-E show how when a given IVC implant 20, having a given, fixed perimeter, is implanted in one or more IVCs having different diameters ranging from 17 to 21 mm, the graft perimeter (2*(20 mm+15.3 mm)=70.6 mm) remains constant and adapts to fit the IVC by changing the arc radii of indentations 48, thereby still maintaining relatively similar IVC-blockage percentages.

For some applications, tubular implant body 40 (e.g., stent frame 70 and fabric 72) is configured such that even when encountering varying diameters of one or more IVCs 30, the unblocked percentage of IVC 30 changes substantially less than the change in overall cross section of IVC 30 (for example, when tubular implant body 40 is fitted in an IVC that varied from 19 mm to 21 mm, the unblocked area would decrease from 31.8% to 29.1% of the original area (an 8% decrease), even though the original area would increase by 22% (from $\pi 9.5$ mm$^2$=284 mm2 to $\pi 10.5$ mm$^2$=346 mm2)).

Figure 8A:
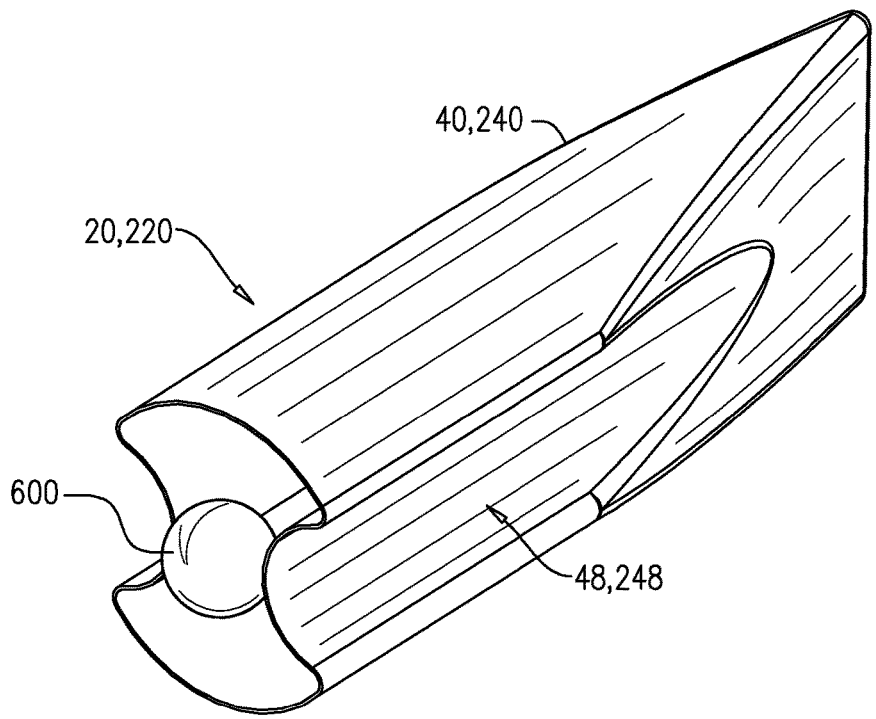
FIG. 8A is a schematic illustration of a technique for mechanically changing the blocked area through the IVC after implantation, in accordance with an application of the present invention.

Reference is made to FIG. 8A, which is a schematic illustration of a technique for mechanically changing the blocked area through the IVC after implantation, such as by expanding a balloon 600 within the tubular section, in accordance with an application of the present invention. When balloon 600 is expanded within the tubular section it presses on indentations 48, 248 making them smaller. Although FIG. 8A shows IVC implant 20, 220 (described hereinabove with reference to FIGS. 3A-B), this balloon-expansion technique may also be used with the other configurations of IVC implant 20 described herein.

Figure 8B:
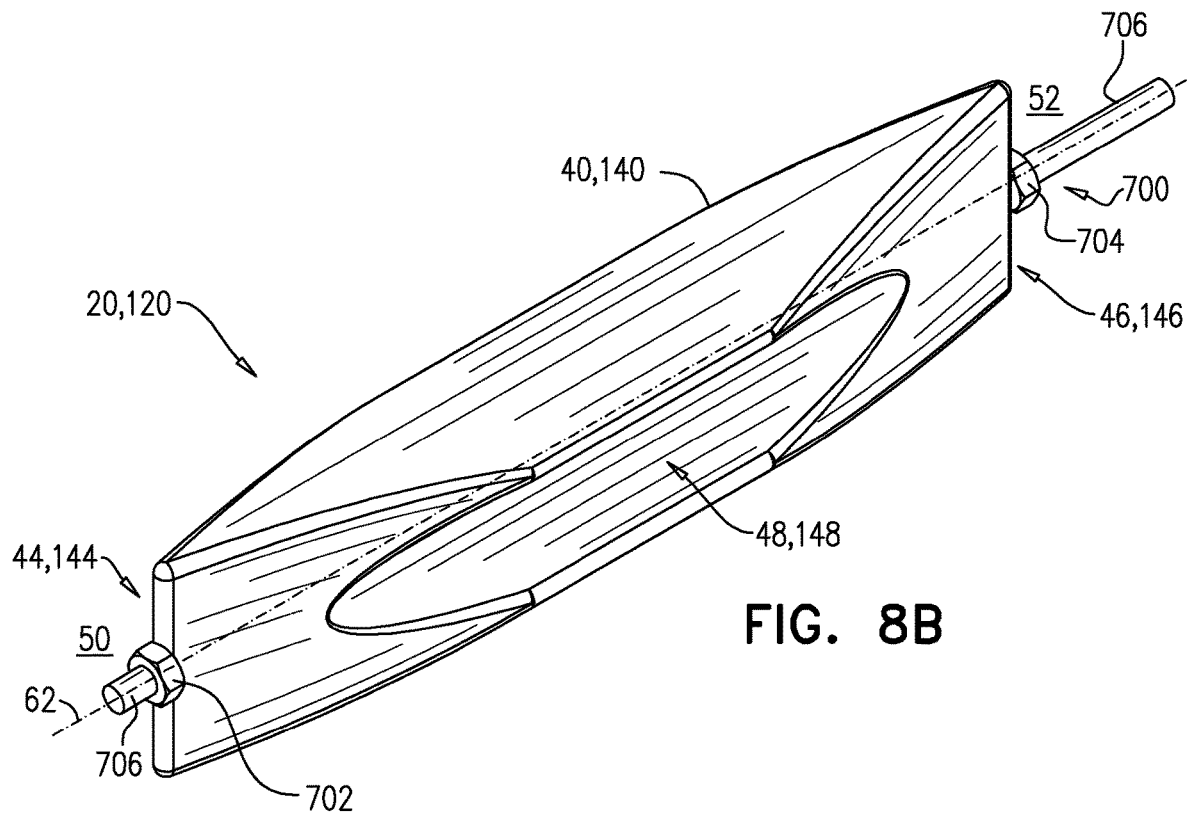
FIG. 8B is a schematic illustration of a technique for changing the pressure drop downstream of an IVC implant, in accordance with an application of the present invention.

Reference is made to FIG. 8B, which is a schematic illustration of a technique for changing the pressure drop downstream 52 of IVC implant 20, 120 by pulling or pushing the tapered upstream end 44, 144 and/or tapered downstream end 46, 146 to change their respective tapers, in accordance with an application of the present invention. The tapers are changed as the tubular length is shortened or lengthened. The tapers may be changed, for example, by pulling a wire, rotating a screw, or inflating a balloon. For example, an adjustment device 700 may comprise one or two nuts 702 and 704 and a screw 706 passing through the nut(s) along central longitudinal axis 62 of tubular implant body 40. Rotation of screw 706 pulls the ends of tubular implant body 40 toward or away from each other, or toward an anchored point at a location between the ends. For some applications, the final blockage percentage of the IVC and the bluntness of the ends of IVC implant 20, 120 is adjustable during and/or after implantation. Thus, for some applications, after tubular implant body 40 is transitioned to the expanded deployment configuration, a degree to which tubular implant body 40 causes pressure loss downstream 52 of IVC implant 20 is adjusted.

Although FIG. 8B shows IVC implant 20, 120 (described hereinabove with reference to FIGS. 1-2B), these taper-adjustment techniques may also be used with the configurations of IVC implant 20 described herein with reference to FIGS. 3A-B and 4A-B.

For some applications, IVC implant 20 comprises one or more pressure transducers for use during implantation or after implantation.

For some applications, tubular implant body 40 comprises radiopaque markers.

In Table I below, the inventor has estimated the final cross-sectional areas, as a percentage of the initial IVC cross sectional area, necessary in order to achieve either a ⅓ drop in pressure or a ½ drop in pressure or a drop to zero pressure. The result depends on the initial pressure (5, 10, 20 and 30 initial pressure as measured in mmHg are shown). The initial average velocity is taken to be 0.2 m/sec and the initial diameter was chosen as 14.5 or 20 mm. Also presented are the equivalent diameters of the two circles that would be passing alongside the respective renal veins (assuming incorrectly that the indentations would be circular). It is noted that greater pressure drops would require smaller final openings, and smaller pressure drops would require larger final openings.

TABLE I

| | | | | | | | | | |
|---|---|---|---|---|---|---|---|---|---|
| | | | | $v_i = .2$ | | | | | |
| | | % $a_i$ open | | | $d_i = 14.5$ $d_f$ (each indent) | | | $d_i = 20$ $d_f$ (each indent) | |
| $p_i$ | $p_f = .66\ p_i$ | $p_f = .5\ p_i$ | $p_f = 0$ | $p_f = .66\ p_i$ | $p_f = .5\ p_i$ | $p_f = 0$ | $p_f = .66\ p_i$ | $p_f = .5\ p_i$ | $p_f = 0$ |
| 5 | 30.5 | 25.1 | 18.1 | 5.7 | 5.2 | 4.4 | 7.8 | 7.1 | 6.0 |
| 10 | 22.1 | 18.2 | 12.9 | 4.8 | 4.4 | 3.7 | 6.6 | 6.0 | 5.1 |
| 20 | 15.7 | 12.9 | 9.2 | 4.1 | 3.7 | 3.1 | 5.6 | 5.1 | 4.3 |
| 30 | 12.9 | 10.6 | 7.5 | 3.7 | 3.3 | 2.8 | 5.1 | 4.6 | 3.9 |

Reference is made to FIGS. 1-8B. Any of the configurations of the upstream ends 44 described herein can be combined with any of the configurations of the downstream ends 46 described herein.

Reference is made to FIGS. 1-8B. Any of the configurations of the upstream ends 44 described herein can be used as a downstream end. Any downstream end can be used as an upstream end.

Reference is made to FIGS. 1-8B. Since in some cases it may be possible to create negative pressures, in some applications IVC implant is deployed in conjunction with one or more stents implanted in the renal veins that prevent their collapsing.

All references made herein to the IVC may alternatively be substituted with a right circular cylinder, which would be used to define geometric properties of the device and not be an element of the invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for implantation in an inferior vena cava (IVC) in a vicinity of junctions between renal veins and the IVC, the apparatus comprising an IVC implant, which comprises a tubular implant body, which is:

configured to assume a compressed delivery configuration and an expanded deployment configuration, and configured such that when implanted in the expanded deployment configuration in the IVC in the vicinity of the renal junctions, (a) has a generally tubular shape, (b) has upstream and downstream ends, and (c) is shaped so as to define:

two indentations on opposite sides of a central portion of the tubular implant body, which have longitudinally-extended shapes so as to allow blood flow in the two indentations from upstream of the tubular implant body to downstream of the tubular implant body, the indentations being configured to be positioned along areas of the vena cava into which blood flows from the renal veins, and wherein the tubular implant body, when in the expanded deployment configuration, narrows from an upstream-most point of the two indentations toward the upstream end of the tubular implant body, and narrows from a downstream-most point of the two indentations toward the downstream end of the tubular implant body, and one or more surfaces that at least partially block blood flow through an interior of the tubular implant body from upstream of the tubular implant body to downstream of the tubular implant body, the one or more surfaces being configured to redirect flow into the indentations, and the indentations being configured to direct the redirected blood to flow longitudinally along the areas of the vena cava into which blood flows from the renal veins, such that velocity of blood flow in the areas of the vena cava into which blood flows from the renal veins is greater than upstream of the tubular implant body, thereby causing a reduction of blood pressure in the renal veins, relative to pressure in the renal veins absent the IVC implant.

2. The apparatus according to claim 1, wherein the tubular implant body is configured such that when implanted in the expanded deployment configuration in the IVC, the one or more surfaces comprise one or more upstream-facing surfaces that face at least partially upstream, and at least partially block blood flow from upstream of the IVC into the interior of the tubular implant body.

3. The apparatus according to claim 2, wherein the tubular implant body is configured such that when implanted in the expanded deployment configuration in the IVC, the one or more surfaces further comprise one or more downstream-facing surfaces that face at least partially downstream, and at least partially block the blood flow between the interior of the tubular implant body and downstream of the tubular implant body.

4. The apparatus according to claim 2, wherein the tubular implant body is configured such that when implanted in the expanded deployment configuration in the IVC, the one or more upstream-facing surfaces entirely block the blood flow from upstream of the IVC into the interior of the tubular implant body.

5. The apparatus according to claim 2, wherein the tubular implant body is configured such that when implanted in the expanded deployment configuration in the IVC, the one or more upstream-facing surfaces comprise exactly one upstream-facing surface.

6. The apparatus according to claim 2, wherein the tubular implant body is configured such that when implanted in the expanded deployment configuration in the IVC, the one or more upstream-facing surfaces comprise a plurality of upstream-facing surfaces.

7. The apparatus according to claim 6, wherein the tubular implant body, when in the expanded deployment configuration, is shaped such that the plurality of upstream-facing surfaces face partially upstream in different respective directions.

8. The apparatus according to claim 1, wherein the tubular implant body is configured such that when implanted in the expanded deployment configuration in the IVC, the one or more surfaces comprise one or more downstream-facing surfaces that at least partially block the blood flow between the interior of the tubular implant body and downstream of the tubular implant body.

9. The apparatus according to claim 8, wherein the tubular implant body is configured such that when implanted in the expanded deployment configuration in the IVC, the one or more downstream-facing surfaces entirely block the blood flow between the interior of the tubular implant body and downstream of the IVC.

10. The apparatus according to claim 8, wherein the tubular implant body is configured such that when implanted in the expanded deployment configuration in the IVC, the one or more downstream-facing surfaces comprise exactly one downstream-facing surface.

11. The apparatus according to claim 8, wherein the tubular implant body is configured such that when implanted in the expanded deployment configuration in the IVC, the one or more downstream-facing surfaces comprise a plurality of downstream-facing surfaces.

12. The apparatus according to claim 1, wherein the tubular implant body is configured such that when in the expanded deployment configuration, the indentations, in cross-section, are shaped as respective smooth curves, the cross-section taken perpendicular to a central longitudinal axis of the tubular implant body.

13. The apparatus according to claim 12, wherein the smooth curves are arcs.

14. The apparatus according to claim 1, wherein the tubular implant body, when in the expanded deployment configuration, is shaped in cross-section so as to define two curved portions that alternate with the indentations around the tubular implant body, the cross-section taken perpendicular to a central longitudinal axis of the tubular implant body at an axial location along the tubular implant body having a greatest cross-sectional area.

15. The apparatus according to claim 14, wherein the two curved portions are two circular arcs.

16. The apparatus according to claim 1, wherein the tubular implant body is configured such that when implanted in the expanded deployment configuration in the IVC, a blood pressure immediately downstream of the tubular implant body is at least 70% of a blood pressure immediately upstream of the tubular implant body.

17. The apparatus according to claim 1, wherein the tubular implant body is configured such that when implanted in the expanded deployment configuration in the IVC, a blood pressure immediately downstream of the tubular implant body is at most 50% of a blood pressure immediately upstream of the tubular implant body.

18. The apparatus according to claim 1, wherein the tubular implant body comprises:
a stent frame; and
a fabric attached to the stent frame.

19. The apparatus according to claim 1,
wherein the tubular implant body, when in the expanded deployment configuration, has a greatest cross-sectional area, taken perpendicular to a central longitudinal axis of the tubular implant body, along an axial portion of the tubular implant body,
wherein the two indentations extend longitudinally at least along the axial portion, and
wherein the axial portion has an axial length of between 3 and 11 cm.

20. The apparatus according to claim 1, wherein the tubular implant body, when in the expanded deployment configuration, has an axial length of between 3 and 20 cm.

21. The apparatus according to claim 1, wherein the tubular implant body, when in the expanded deployment configuration, other than the indentations, is shaped as two circular arcs of a circle in cross-section, the cross-section taken perpendicular to a central longitudinal axis of the tubular implant body at an axial location along the tubular implant body having a greatest cross-sectional area.

22. The apparatus according to claim 21, wherein the tubular implant body, when in the expanded deployment configuration, has a greatest cross-sectional area at the axial location along the tubular implant body, the greatest cross-sectional area equal to between 70% and 95% of the area of the circle.

23. The apparatus according to claim 21, wherein the circle has a diameter of between 1.3 and 3.5 cm.

24. The apparatus according to claim 1, wherein the tubular implant body, when implanted in the expanded deployment configuration, is shaped so as to allow approximately equal blood flow in the two indentations from upstream of the tubular implant body to downstream of the tubular implant body.

* * * * *